US010426649B2

(12) United States Patent
Lyu

(10) Patent No.: US 10,426,649 B2
(45) Date of Patent: Oct. 1, 2019

(54) POSTURE IMPROVEMENT SHAPEWEAR GARMENT AND SYSTEMS

(71) Applicant: Saemee Lyu, St. Paul, MN (US)

(72) Inventor: Saemee Lyu, St. Paul, MN (US)

(*) Notice: Subject to any disclaimer, the term of this patent is extended or adjusted under 35 U.S.C. 154(b) by 826 days.

(21) Appl. No.: 14/924,261

(22) Filed: Oct. 27, 2015

(65) Prior Publication Data

US 2016/0113806 A1 Apr. 28, 2016

Related U.S. Application Data

(60) Provisional application No. 62/069,646, filed on Oct. 28, 2014.

(51) Int. Cl.
*A61F 5/02* (2006.01)
*A41B 9/08* (2006.01)
*A41B 9/16* (2006.01)
*A41D 13/00* (2006.01)

(52) U.S. Cl.
CPC ............... *A61F 5/026* (2013.01); *A41B 9/08* (2013.01); *A41B 9/16* (2013.01); *A41B 2400/38* (2013.01); *A41D 13/0015* (2013.01)

(58) Field of Classification Search
CPC ......... A41B 2400/38; A41B 9/08; A41B 9/16; A41C 1/003; A41C 1/12; A61F 5/026
USPC .................................... 450/151, 155, 95, 96
See application file for complete search history.

(56) References Cited

U.S. PATENT DOCUMENTS

| 2,317,819 | A | * | 4/1943 | Smith | A41B 9/08 |
| | | | | | 2/407 |
| 2,443,316 | A | | 6/1948 | Israel | |
| 4,698,847 | A | | 10/1987 | Yoshihara | |
| 5,699,559 | A | | 12/1997 | Sano | |
| 5,857,947 | A | * | 1/1999 | Dicker | A63B 21/00185 |
| | | | | | 2/69.5 |
| 5,996,120 | A | | 12/1999 | Balit | |
| 7,395,557 | B1 | | 7/2008 | Ledyard | |
| 7,546,751 | B2 | * | 6/2009 | Lutz | A41B 9/00 |
| | | | | | 66/171 |
| 8,230,520 | B2 | * | 7/2012 | Riondato | A41D 1/084 |
| | | | | | 2/275 |
| 8,425,275 | B2 | | 4/2013 | Noel | |
| 8,549,763 | B2 | | 10/2013 | Krawchuk | |
| 2012/0179080 | A1 | | 7/2012 | Sakamoto et al. | |

* cited by examiner

*Primary Examiner* — Alissa J Tompkins
*Assistant Examiner* — Brieanna Szafran
(74) *Attorney, Agent, or Firm* — Fish & Richardson P.C.

(57) ABSTRACT

Shapewear garments and garment systems are provided for comfortable yet effective postural and body shape improvement. The shapewear garment as described herein includes a plurality of support bands on a rear portion of a torso body of the shapewear garment to provide effective support for different areas of the back and spine to achieve more balanced posture as well as a psychological boost from a slimmer, smoother body shape.

20 Claims, 29 Drawing Sheets

POSTURE IMPROVEMENT SHAPEWEAR GARMENT AND SYSTEMS

CROSS-REFERENCE TO RELATED APPLICATION(S)

This application claims the benefit of U.S. Patent Application Ser. No. 62/069,646, filed Oct. 28, 2014, the entirety of which is hereby incorporated by reference.

BACKGROUND

Some people tend to transform their physical appearances to prevent low self-esteem due to body image attitudes that may be based on how the media portrays the body. There have been many attempts to develop body shaping products that address this issue and provide a body shape which is slim and curvy. For example, some shapewear garments transform a body silhouette and create an illusion of an hourglass figure. Some shapewear garments may have negative effects on health, such as gastric reflux and compressed stomach or intestines. Many women may wear shapewear garments to improve body appearance even though the shapewear garment may be uncomfortable and provide these negative effects. However, some types of shapewear garments or corsets may actually improve body posture and ease back pain.

Human posture may be an important factor in improving body image because poor posture may make a person feel tired, ill, and unattractive. Many products have been designed to improve posture called posture correctors or back supporters. However, these products may be uncomfortable due to rigid materials that stress skin and limit mobility making everyday use of these products difficult.

SUMMARY

In general terms, this disclosure is directed to shareware garments and garment systems for posture improvement. In one possible configuration and by non-limiting example, the shareware garment includes a plurality of support bands attached on a rear portion of the garment. Various aspects are described in this disclosure, which include, but are not limited to, the following aspects.

One aspect is a garment including a torso body and a plurality of support bands. The torso body has a front portion and a rear portion and includes a neck opening, a right arm opening, a left arm opening, a right leg opening, a left leg opening, a waist region, a right underarm region, and a left underarm region. The waist region is located around the torso body between the arm openings and the leg openings and includes a left waist region, a right waist region, and a low waist region between the left and right waist regions. The low waist region includes an area of the shapewear garment that is located on or adjacent the lumbar vertebrae 1 to 5 (L1-L5) of a wearer. The right underarm region is located adjacent the right arm opening between the right arm opening and the right leg opening. The left underarm region is located adjacent the left arm opening between the left arm opening and the left leg opening. The plurality of support bands is attached to the rear portion of the torso body. Each support band extends between (1) one of the neck opening, the right arm opening, the left arm opening, the right leg opening, the left leg opening, the left waist region, the right waist region, the low waist region, and right underarm region, and the left underarm region and (2) another of the neck opening, the right arm opening, the left arm opening, the right leg opening, the left leg opening, the left waist region, the right waist region, the low waist region, and right underarm region, and the left underarm region. Further, at least two of the support bands intersect at an intersection on the rear portion of the torso body.

In certain examples, the plurality of support bands includes first, second, third, and fourth support bands. The first support band extends from the left underarm region toward the right waist region on the rear portion of the torso body. The second support band extends from the right underarm region toward the left waist region on the rear portion of the torso body. The first support band and the second support band intersect proximate an intersection. The third support band extends from the low waist region toward the neck opening on the rear portion of the torso body. The fourth support band extends from a first location between the right shoulder strap region and the right underarm region toward a second location between the left shoulder strap region and the left underarm region on the rear portion of the torso body.

In certain examples, the plurality of support bands includes first, second, third, fourth, and fifth support bands. The first support band extends from the left underarm region toward the right waist region on the rear portion of the torso body. The second support band extends from the right underarm region toward the left waist region on the rear portion of the torso body. The first support band and the second support band intersect proximate an intersection. The third support band extends from the low waist region toward the neck opening on the rear portion of the torso body. The fourth support band extends between the right shoulder strap region and left shoulder strap region on the rear portion of the torso body. The fifth support band extends from the first location between the right shoulder strap region and the right underarm region toward the second location between the left shoulder strap region and the left underarm region on the rear portion of the torso body.

In certain examples, the plurality of support bands includes first, second, third, fourth, and fifth support bands. The first support band extends from the left underarm region toward the right waist region on the rear portion of the torso body. The second support band extends from the right underarm region toward the left waist region on the rear portion of the torso body. The first support band and the second support band intersect proximate an intersection. The third support band extends from the low waist region toward the neck opening on the rear portion of the torso body. The fourth support band extends from the right shoulder strap region toward a third location between the left arm opening and the left leg opening on the rear portion of the torso body. The fifth support band extends from the left shoulder strap region toward a fourth location between the right arm opening and the right leg opening on the rear portion of the torso body.

In certain examples, the plurality of support bands includes first, second, third, fourth, and fifth support bands. The first support band extends from the left underarm region toward the right waist region on the rear portion of the torso body. The second support band extends from the right underarm region toward the left waist region on the rear portion of the torso body. The first support band and the second support band intersect proximate an intersection. The third support band extends from the low waist region toward the neck opening on the rear portion of the torso body. The fourth support band extends from the right shoulder strap region toward the fourth location between the right arm opening and the right leg opening on the rear portion of the torso body. The fifth support band extends from the left shoulder strap region toward the third location between the left arm opening and the left leg opening on the rear portion of the torso body.

In certain examples, the plurality of support bands includes first, second, third, fourth, fifth, and sixth support bands. The first support band extends from the left underarm region toward the right waist region on the rear portion of the torso body. The second support band extends from the right underarm region toward the left waist region on the rear portion of the torso body. The first support band and the second support band intersect proximate an intersection. The third support band extends from the low waist region toward the neck opening on the rear portion of the torso body. The fourth support band extends between the right and left arm opening on the rear portion of the torso body. The fifth support band extends from the fourth support band toward a right shoulder strap region on the rear portion of the torso body. The sixth support band extends from the fourth support band toward a left shoulder strap region on the rear portion of the torso body. The fifth and sixth support bands are transverse to the fourth support band.

Another aspect is a garment system including the garment described herein and a brief panty. The brief panty includes a waist support band positioned around a waist of the brief panty, and the brief panty defines an inside of the brief panty and an outside of the brief panty. In certain examples, the waist support band is folded downward from the waist of the brief panty and on the inside of the brief panty.

DETAILED DESCRIPTION

Figure 1:
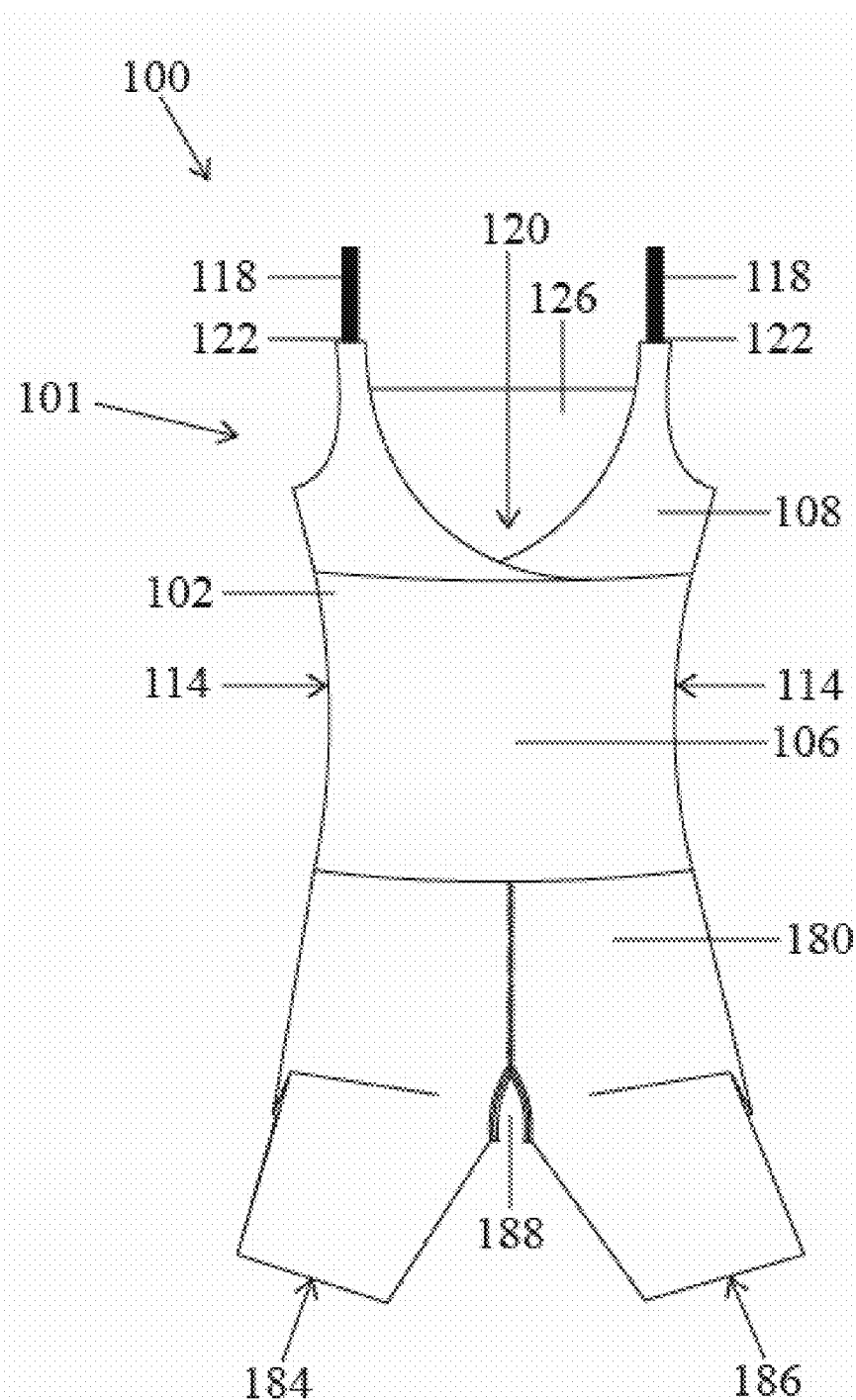
FIG. 1 illustrates a front view of one embodiment of a shapewear garment.

Various embodiments will be described in detail with reference to the drawings, wherein like reference numerals represent like parts and assemblies throughout the several views.

The present disclosure relates generally to shapewear garments and garment systems for posture improvement.

Soft structural support shapewear garments and garment systems as described herein may provide effective support in improving posture and body shape.

Some embodiments described herein include a shapewear garment including a torso body configured to be worn around at least a portion of a human body (e.g., torso, full body, from upper back to mid-thigh, etc.). In some embodiments, at least some embodiments of the shapewear garment 100 according to the present disclosure may be applied to an existing product (e.g., a "Self Expressions" bodysuit by Maidenform Brands, etc.). In other embodiments, the shapewear garment may be specifically designed and manufactured as described herein. The shapewear garment may feature an open bust area so that a person may wear their own bra in addition to the shapewear garment. The type of shapewear garment used may be based on the shapewear garment being designed to, e.g., provide overall definition to the middle part of the body, lift the hips, flatten the tummy and/or provide a defined waistline. In some embodiments, the shapewear garment may be a part of a garment system that includes a separate brief panty. The shapewear garment may include a plurality of openings (e.g., neck opening, right arm opening, left arm opening, right leg opening, left leg opening, lower body opening, crotch opening, etc.) to allow the shapewear garment to be configured to be worn on the human body. The shapewear garment may also include a variety of garment foundations (e.g., one-piece, torso/back panel, etc.).

In some embodiments, the shapewear garment may include notable regions (e.g., waist region, right underarm region, left underarm region, etc.) to assist in construction of the shapewear garment. The waist region may be located around the torso body of the shapewear garment between the arm openings and the leg/lower body openings, generally in a waist area of the human body. The waist region may include a right waist region, a left waist region and a low waist region between the right and left waist regions. In this document, the low waist region can include a region of the shapewear garment that is located on or adjacent the lumbar vertebrae 1 to 5 (L1-L5) of a wearer. The right underarm region may be located between the right arm opening and the right leg opening and closer to the right arm opening than the right leg opening. The left underarm region may be located between the left arm opening and the left leg opening and closer to the left arm opening than the left leg opening.

Figure 2:
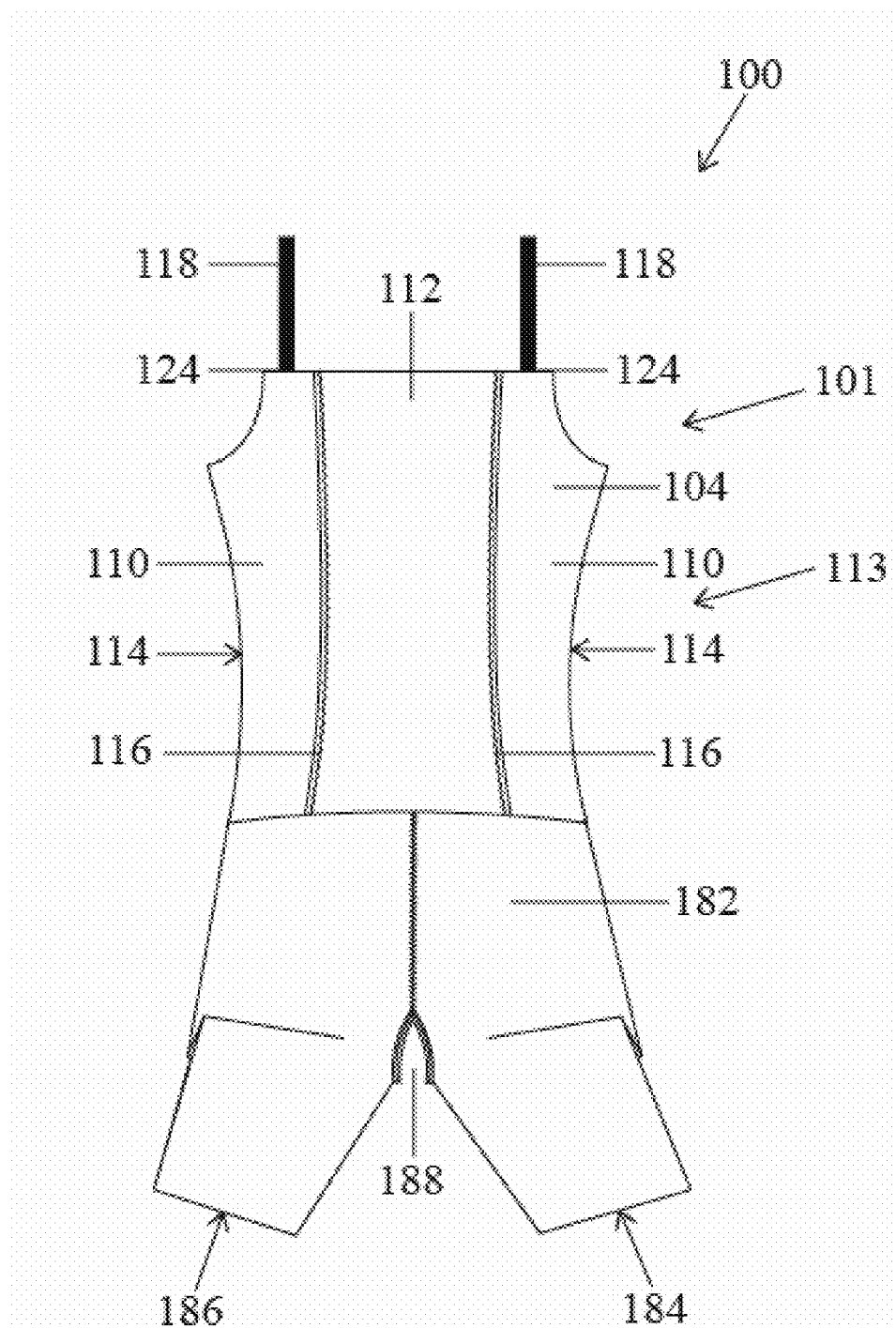
FIG. 2 illustrates a rear view of the shapewear garment of FIG. 1.

FIGS. 1 and 2 illustrates a front and rear view of one embodiment of a shapewear garment 100. The shapewear garment 100 may include a torso body 101 having a front portion 102 and a rear portion 104 that are configured to be positioned on the front and rear portion of a human body, respectively. In some embodiments, the front and rear portions 102, 104 may define a tubular article configured to fit on the torso of a wearer. The front portion 102 of the shapewear garment 100 may include a front torso panel 106 and an open-bust panel 108. The open-bust panel 108 may be made of a stretchable fabric (e.g., 80% nylon and 20% spandex/elastane, etc.). The front torso panel 106 may also be made of a stretchable fabric (e.g., about 80% nylon and about 20% spandex/elastane, etc.).

The fabric used to construct the shapewear garment 100 may have any suitable firmness characteristic and the illustrative examples of fabrics specifically identified herein are only examples of the multitude of other fabrics that may be used in connection with the shapewear garments 100 described herein. The rear portion 104 may include multiple back torso side panels 110 and a center back princess panel 112 (collectively, the back torso side panels 110 and the center back princess panel 112 can be referred to herein as a back torso panel 113). The rear portion 104 may be made of similar or different fabrics from the front portion 102 or the front torso panel 106. The front torso panel 106 may be connected to each back torso side panel 110 along a seam. The center back princess panel 112 may be connected to each back torso side panel 110 along a seam 116. The seam 116 may be stitched (e.g., single top zigzag stitch, etc.) to secure the panels to each other while potentially adding decoration and/or extra strength to the shapewear garment 100. The seams 116 may also provide added tension to the front and rear portions 102, 104.

As shown in FIGS. 1 and 2, the shapewear garment 100 may include a shoulder strap 118 on each side of a neck opening 120. A first end 122 of the shoulder strap 118 may be attached to the front portion 102 and a second end 124 of the shoulder strap 118 may be attached to the rear portion 104. The first end 122 of the shoulder strap 118 may be attached to the front torso panel 106 or the open-bust panel 108. The second end 124 of the shoulder strap 118 may be attached to the back torso side panel 110 or the center back princess panel 112. The shoulder straps 118 may be attached to the shapewear garment 100 by, e.g., stitches, fasteners, buttons, snaps, etc. In some embodiments, the shoulder straps 118 may be made of, e.g., elastic trim materials, etc. The shoulder straps 118 may include any suitable width, e.g., about 2 inches, about 1 inch, about 0.6 inches, or about 0.4 inches. In other embodiments, the shoulder straps 118 may be one continuous portion of material with the rest of the shapewear garment 100 (see, e.g., FIGS. 11-14).

In some embodiments, the shapewear garment 100 may include a back torso lining 126 inserted into the inside of the back torso panel 113. The torso lining 126 may be made of, e.g., polyester, etc. In one or more embodiments, the torso lining 126 may be constructed of a stretchable and thin fabric.

The shapewear garment 100 may include support bands positioned on the rear portion 104 of the shapewear garment 100. In some embodiments, the shapewear garment 100 may include less than four support bands. In other embodiments, the shapewear garment 100 includes four support bands. In yet other embodiments, the shapewear garment 100 includes more than four support bands.

The shapewear garment 100 may include one or more support bands positioned on the rear portion 104 of the shapewear garment 100 in various manners. In some embodiments, the support bands may be integrated into the back torso lining 126 or the back torso panels (including the back torso side panels 110 and the center back princess panel 112). In other embodiments, the support bands may be attached to the back torso lining 126. In other embodiments, the support bands may be attached to the back torso panels. In other embodiments, the support bands may be located in between the back torso lining 126 and the back torso panels. In other embodiments, the support bands are positioned outside of the rear torso panels. In yet other embodiments, the support bands can be positioned in other locations.

The support bands may include any suitable width, e.g., about 3 inches, about 2 inches, about 1 inch, about 0.5 inches, etc. In some embodiments, the support bands may be made of the same fabric as the shapewear garment 100. In other embodiments, the support bands can be made of a different fabric than the shapewear garment 100. In some embodiments, the support bands can be made of, e.g., about 68% nylon and 32% spandex/elastane. In other embodiments, the support bands can be made of stretchable materials. In yet other embodiments, the support bands can be made of elastic trims. Other materials are also possible. In some embodiments, the support bands may define a shape that is, e.g., straight, bent, curved, or shaped in a way conducive to support. In some embodiments, the support bands may define a cross-sectional shape (e.g., square, circle, rectangular, etc.).

Figure 3A:
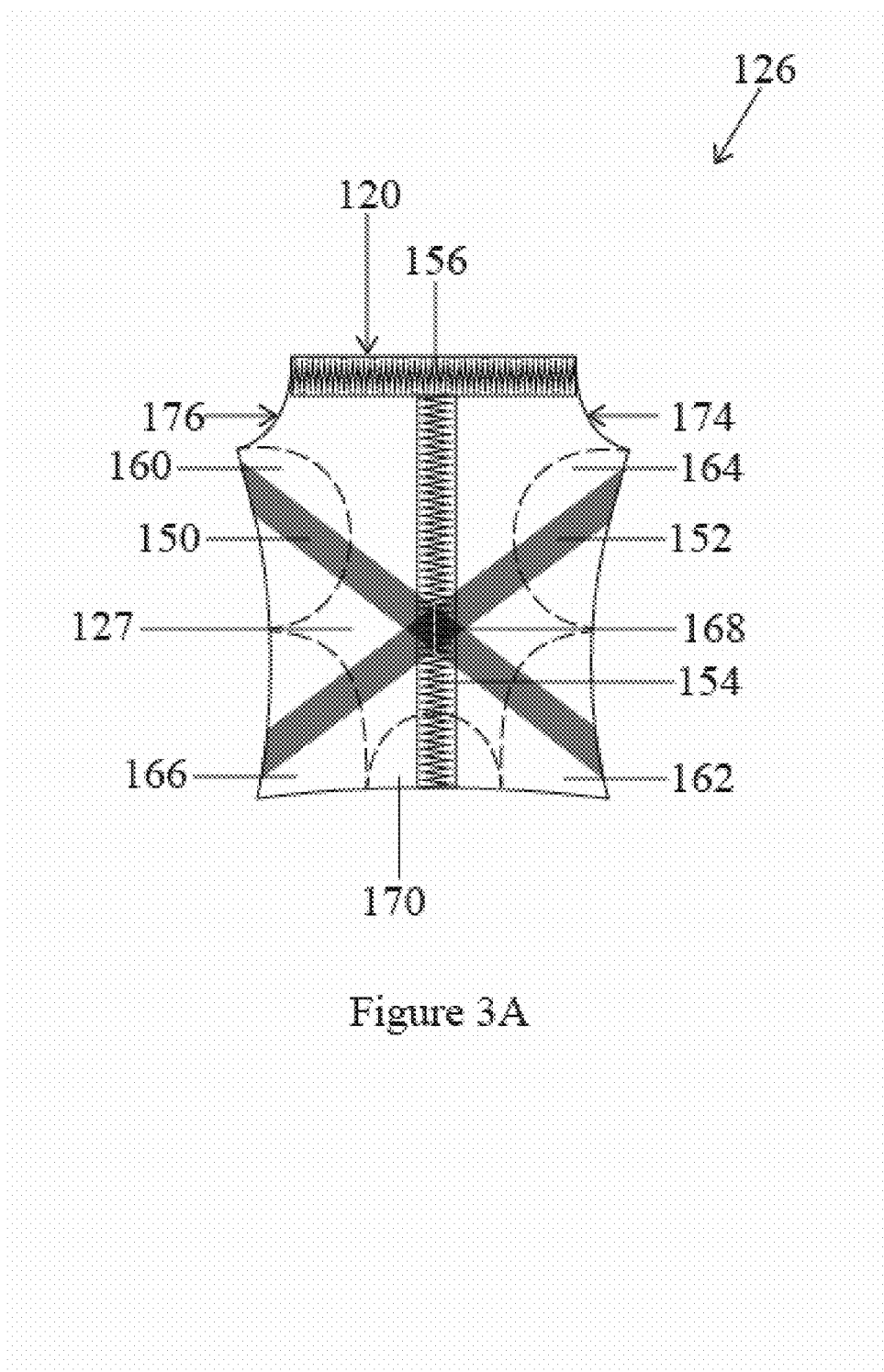
FIG. 3A illustrates an inside view of one embodiment of a back torso lining of a shapewear garment including four support bands.
Figure 3B:
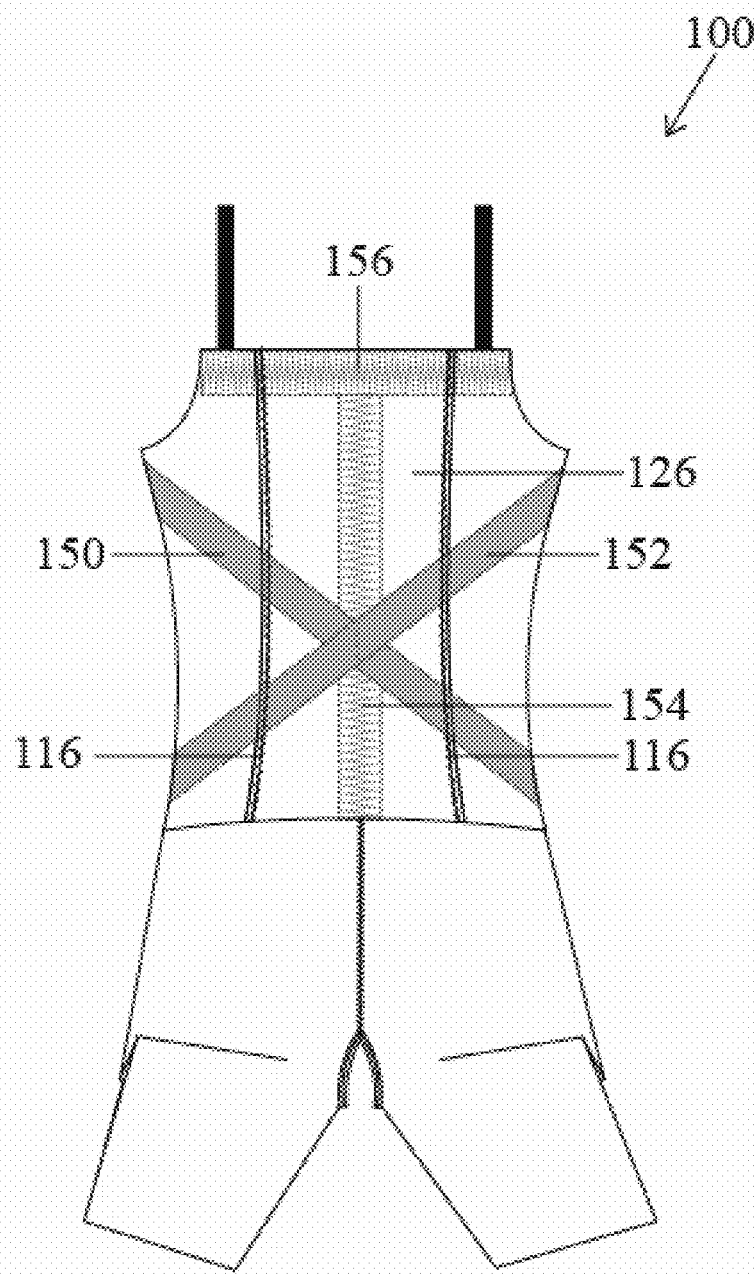
FIG. 3B illustrates a rear view of one embodiment of a full-length shapewear garment including the back torso lining to illustrate the locations of the back support bands.

As shown in FIGS. 3A and 3B, the depicted illustrative embodiments of the shapewear garment 100 may include four support bands 150, 152, 154, and 156. In this example, it is illustrated that the support bands are attached to the back torso lining 126 (e.g., an inside 127 thereof), and the back torso lining 126 is then attached to, or inserted into, the rear portion 104 of the torso body 101, as shown in FIG. 3B. However, the support bands can be positioned on the rear portion 104 of the torso body 101 in various manners as described above.

A first support band 150 of the four support bands may extend from a left underarm region 160 toward a right waist region 162 on the rear portion 104 of the torso body 101. A second support band 152 of the four support bands may extend from a right underarm region 164 toward a left waist region 166 on the rear portion 104 of the torso body 101. In some embodiments, the first and second support bands 150, 152 may extend all the way from a seam 114 on one side of the shapewear garment 100 to a seam 114 on the opposite side of the shapewear garment 100. The first and second support bands 150, 152 may intersect at an intersection point 168 so that the first and second support bands 150, 152 may define, e.g., an X-shape. In some embodiments, the first and second support bands 150, 152 may be substantially transverse to one another proximate the intersection 168.

A third support band 154 of the four support bands may extend from a low waist region 170 toward a center of the neck opening 120 on the rear portion 104 of the torso body 101. In some embodiments, the third support band 154 may be oriented such that the third support band 154 is substantially vertical when a wearer is standing upright. In some embodiments, the third support band 154 is arranged such that, when the shapewear garment 100 is worn, the third support band 154 extends from the upper spine region (e.g., cervical vertebra 7, C7) to the lower spine region (e.g., lumbar vertebra 5, L5) of a wearer.

A fourth support band 156 of the four support bands may extend between the right and left arm openings 174, 176 on the rear portion 104 of the torso body 101. In some embodiments, the fourth support band 156 may be oriented such that the fourth support band 156 is substantially horizontal when a wearer is standing upright. In one or more embodiments, the third and fourth support bands 154, 156 may be transverse to one another. As used herein to describe the orientation of bands and other components with respect to each other, the term "transverse" can include perpendicular as well as nearly perpendicular (e.g., ±10 degrees from perpendicular). In some embodiments, the third and fourth support bands 154, 156 define, e.g., a T-shape. The T-shape defined by the third and fourth support bands 154, 156 may provide support to the spine to help with scoliosis by potentially improving abnormal curvatures of the spine. The first and second support bands 150, 152 may provide a dual support to the spine curvature when placed on the third and fourth support bands 154, 156 (e.g., the X-shape defined by the first and second support bands 150, 152 in combination with the T-shape defined by the third and fourth support bands 154, 156).

In some embodiments, the first and second support bands 150, 152 may be attached together at or proximate the intersection 168. The first and second support bands 150, 152 may be attached (e.g., stitched) together at or proximate the intersection 168 as well as to one or more other components of the shapewear garment 100 (e.g., the third support band 154, the back torso lining 126, the center back princess panel 112, the back torso panel 113 (e.g., the back torso side panels 110 and the center back princess panel 112), etc.). In some embodiments, the intersection 168 may be located, e.g., on the third support band 154, to the left of the third support band 154, to the right of the third support band 154, closer to the neck opening 120 than a waist region 171 (which can include the right waist region 162 and the left waist region 166), closer to the waist region 171 than the neck opening 120, in the middle between the neck opening 120 and the waist region 171, etc. The placement of the intersection 168 proximate one of these locations may provide increased stability to the support bands and the shapewear garment 100. In one or more embodiments, the first and second support bands 150, 152 may be attached (e.g., stitched, etc.) at the intermediate locations of each band on the shapewear garment 100 (e.g., back torso lining 126, the center back princess panel 112, the back torso panel 113, etc.) to prevent rolling up of the bands due to friction while wearing the garment.

In one or more embodiments, the support bands used to construct the shapewear garments described herein may have a modulus of elasticity that is greater than the modulus of elasticity of the fabric or fabrics used to construct the torso body to which the support bands are attached (where the fabric or fabrics are of the same width as the support bands—with width being measured transverse to the direction of elongation). In other words, the resistance to elastic elongation along their length of the support bands is greater than the resistance to elastic elongation of the underlying fabric to which the support bands are attached in one or more embodiments. Further, the support bands used in the same garment may have different moduli of elasticity.

Figure 4:
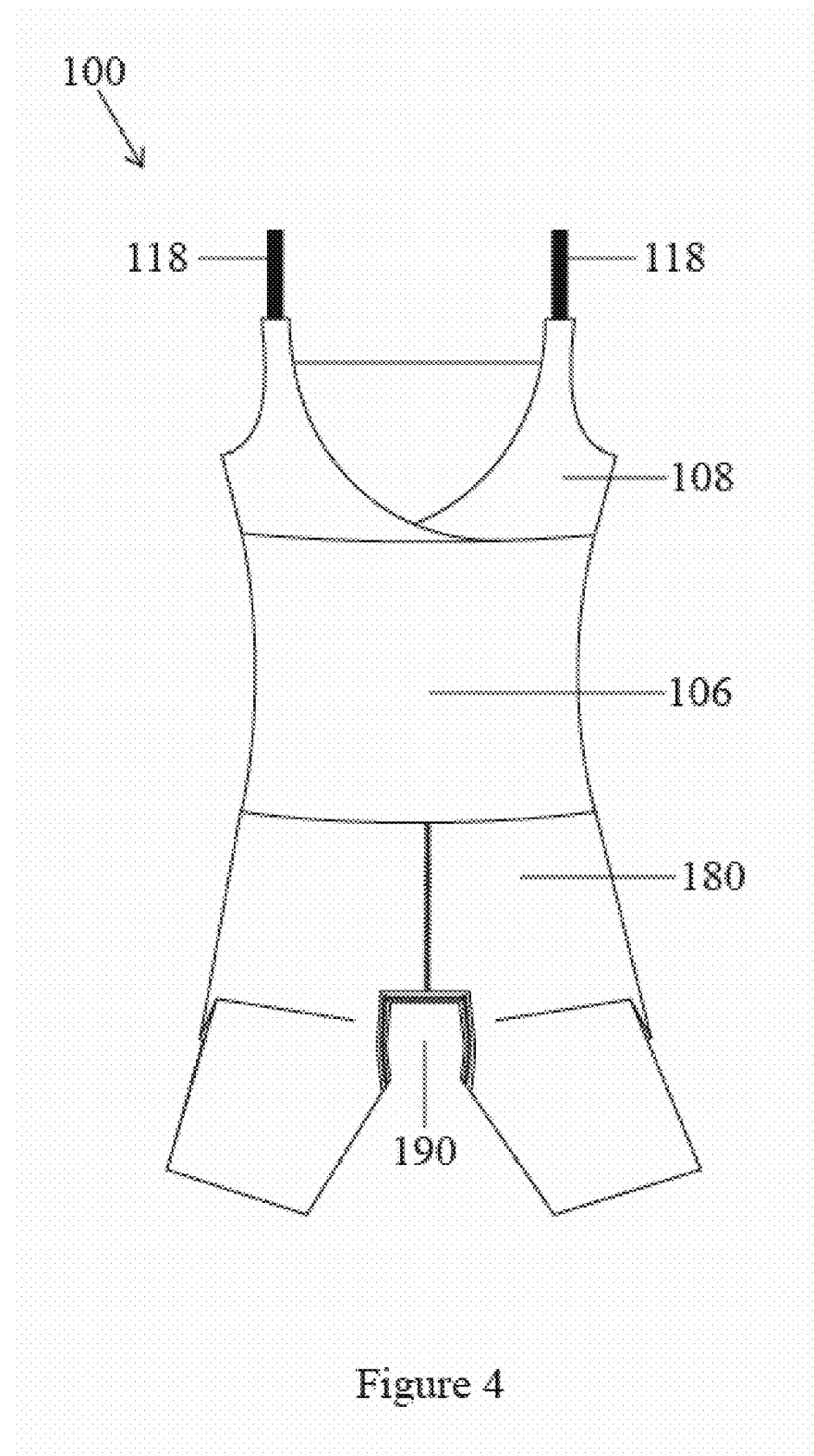
FIG. 4 illustrates a front view of one embodiment of a shapewear garment including a wide opening crotch.
Figure 5:
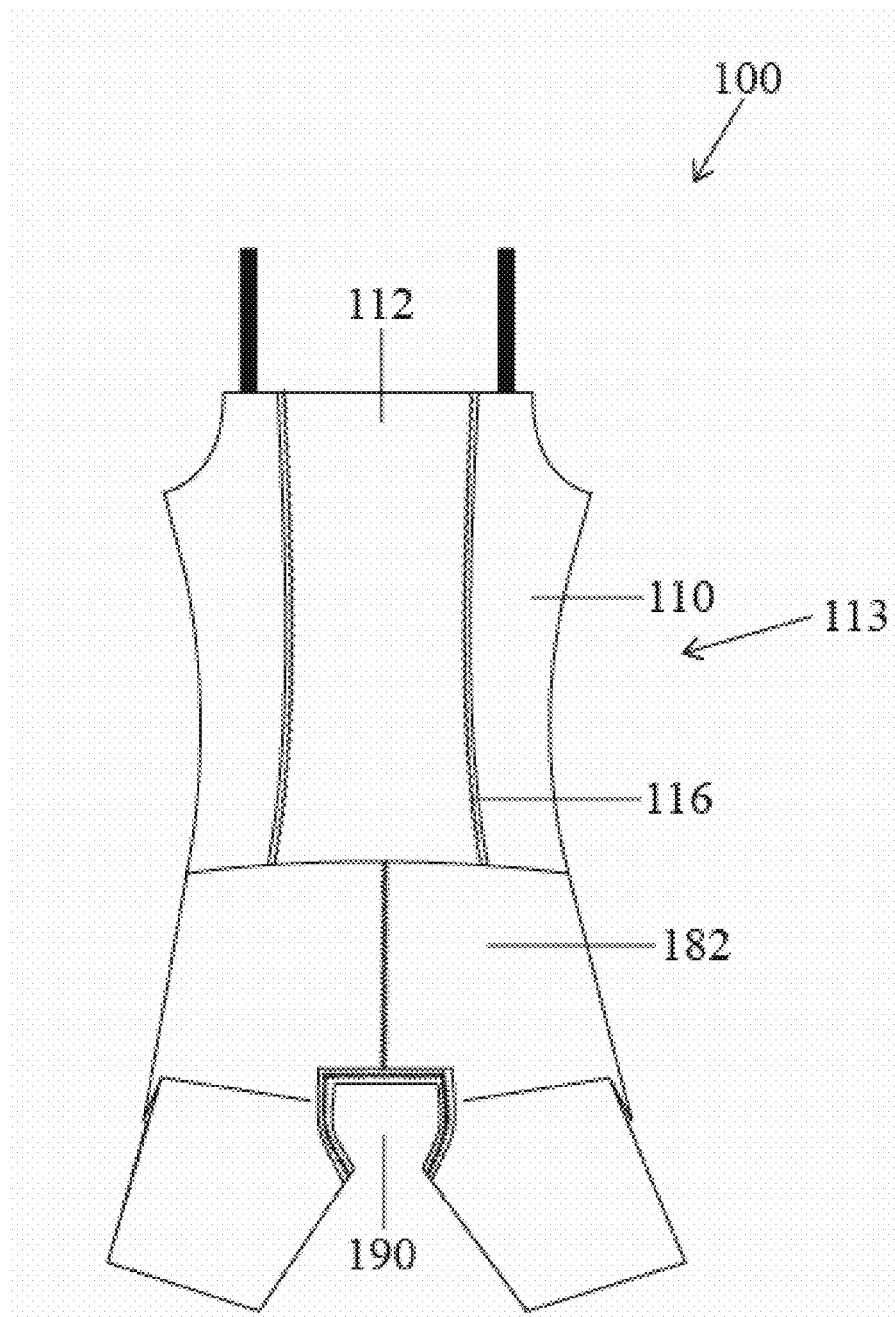
FIG. 5 illustrates a rear view of the shapewear garment of FIG. 4.
Figure 6:
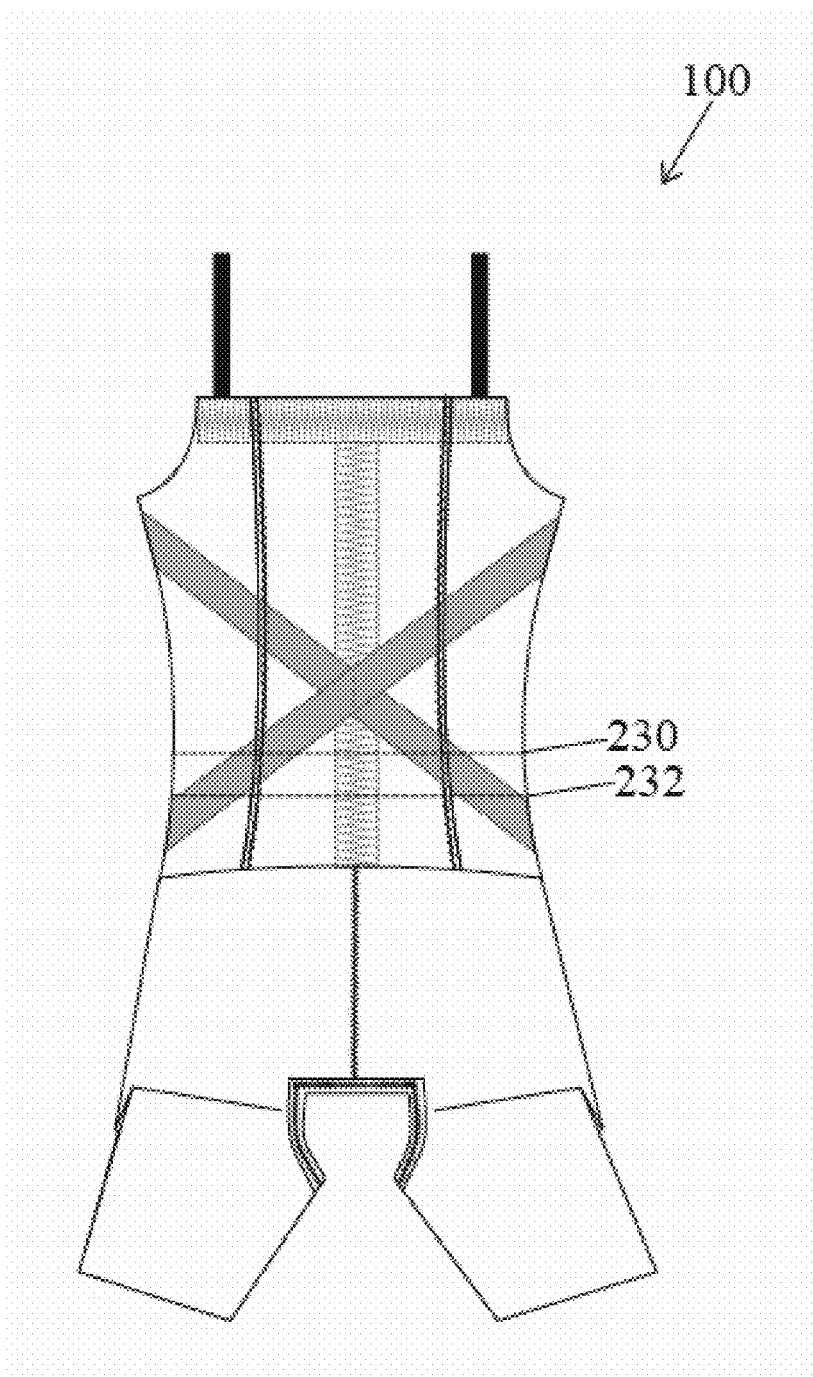
FIG. 6 illustrates the rear view of one embodiment of a full-length shapewear garment including a back torso lining to illustrate locations of back support bands as well as waist and abdomen support locations of an optional brief panty.

As shown in FIGS. 1 and 2, the shapewear garment 100 may include a front bottom panel 180 and a back bottom panel 182. The front and back bottom panels 180, 182 may be attached to the torso panels defining the torso body as described herein. The front and back bottom panels 180, 182 may define a right leg opening 184 and a left leg opening 186. In some embodiments, the front and back bottom panels 180, 182 may define an opening crotch 188 for toileting use. As shown in FIGS. 4-6, the shapewear garment 100 may include a wide opening crotch 190.

As shown in FIGS. 7A, 7B, 8, 9A, and 9B, in some embodiments, the shapewear garment 100 may be part of a garment system 200 that also may include a brief panty 202. The brief panty 202 may be worn along with the shapewear garment 100 and may or may not be permanently attached to the shapewear garment 100 (where permanent attachment requires destruction of a seam or other attachment in a manner that cannot be reversed). In some embodiments, the brief panty may include any lower body garment (e.g., panty hose, corsets, leggings, boxer briefs, boxer shorts, gym wear to prevent injury, etc.). The brief panty may include a closed crotch that is capable of covering the crotch opening when worn with the shapewear garment 100. The brief panty may also be capable of smoothing body bulges and improving posture when worn on the body. In some embodiments, the panty brief may be, e.g., the same materials as the shapewear garment 100, different materials than the shapewear garment 100, etc.

As shown in FIGS. 7A, 7B, 9A, and 9B, the brief panty 202 may include a front portion 204 and a rear portion 206. The rear portion 206 of the brief panty may include a first panel 208 and a second panel 210 attached (e.g., sewn, etc.) to each other. The front portion 204 of the brief panty 202 may include a front panty panel 212. The first and second panels 208, 210 may be attached to the front panty panel 212. The brief panty 202 may include a crotch strap 214 that may be seamed proximate the front panty panel 212 along a line 216 including, e.g., a stitch (e.g., a single top zigzag stitch, a straight stitch, etc.). The brief panty 202 may further include a cotton panel 218 that may be secured to an inside bottom of the brief panty to provide physiological comfort.

The brief panty 202 may include a waist support band 220 positioned around a waist of the brief panty. The waist support band 220 may be made of, e.g., the same materials as the support bands of the shapewear garment 100, different materials than the support bands of the shapewear garment 100 (e.g., about 68% nylon and 32% spandex/elastane, etc.). The use of a similar material may provide a comparable amount of support as the support bands. However, the use of a different material that may be, e.g., thicker and stronger than the support bands of the shapewear garment 100 material, may provide increased posture support. The waist support band 220 may include any suitable width, e.g., about 4 inches, about 3 inches, about 2 inches, about 1 inch, about 0.5 inches, etc. In some embodiments, the waist support band 222 may be folded down on an inside of the brief panty 202 (see, e.g., FIGS. 9A and 9B).

Figure 8:
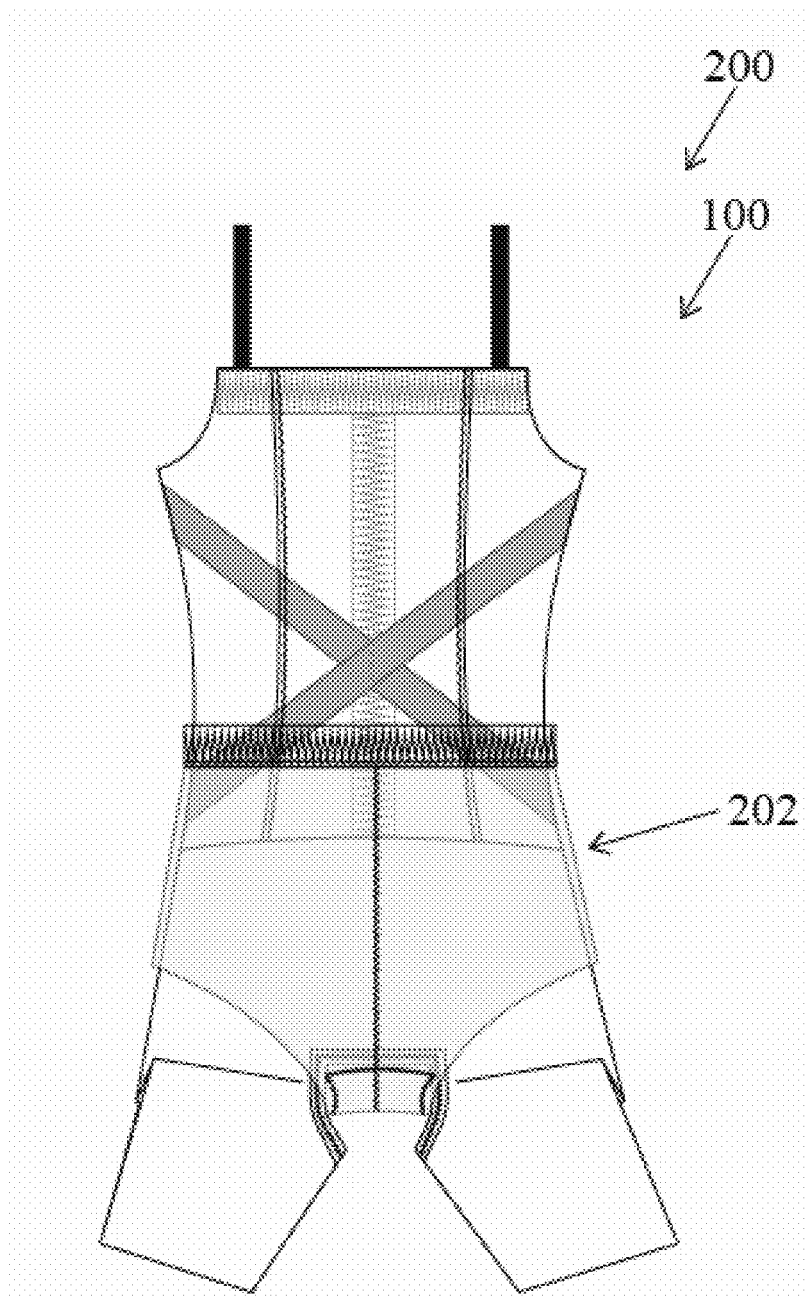
FIG. 8 illustrates a rear view of one embodiment of a shapewear garment and the brief panty placed over the shapewear garment to support the waist.
Figure 9A:
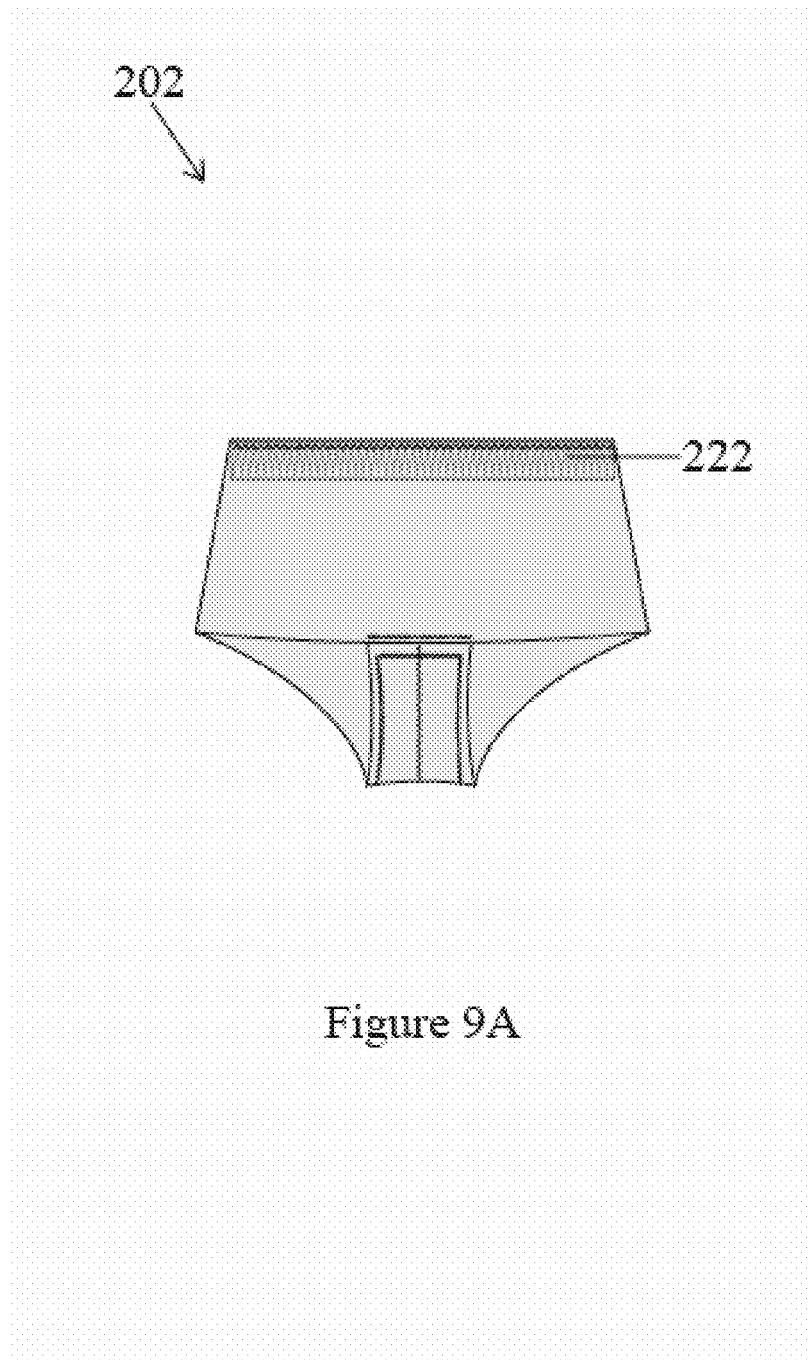
FIG. 9A illustrates a front view of the brief panty of FIG. 7A, having the support waist band folded downwardly from a waist line to an inside of the panty around an abdomen line.
Figure 9B:
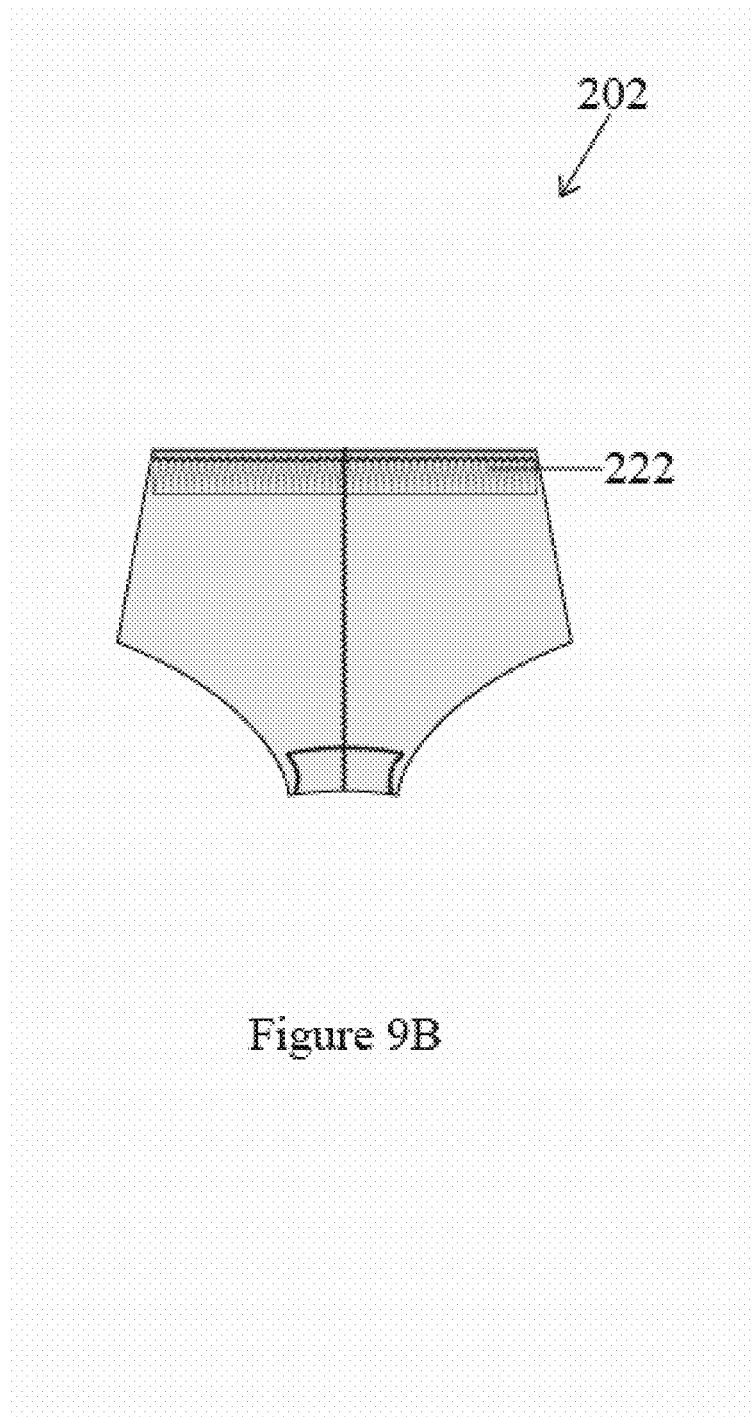
FIG. 9B illustrates a rear view of the brief panty element of FIG. 9A.

As shown in FIG. 6, the shapewear garment 100 may define a waist line 230 and an abdomen line 232. In some embodiments, the abdomen line 232 is arranged below the waist line 230. For example, the abdomen line 232 may be three inches below the waist line 230 when in an elevated use position of the brief panty. The waist support band 220, 222 on the brief panty 202 may be located at or proximate the waist line 230 when the brief panty and shapewear garment 100 are worn together, as shown in FIG. 8. The waist support band may be folded downward from the waist of the brief panty and on an inside of the brief panty to help smooth body bulges and improve posture around an abdomen area, as shown in FIG. 9. In some embodiments, the waist support band 220, 222 may be located proximate the abdomen line 232 when folded downward. The presences of the waist support band may provide additional back and spine support and create a "triple back support" when combining the waist support band and the X-shape and T-shape defined by the four support bands of the shapewear garment 100.

Figure 11:
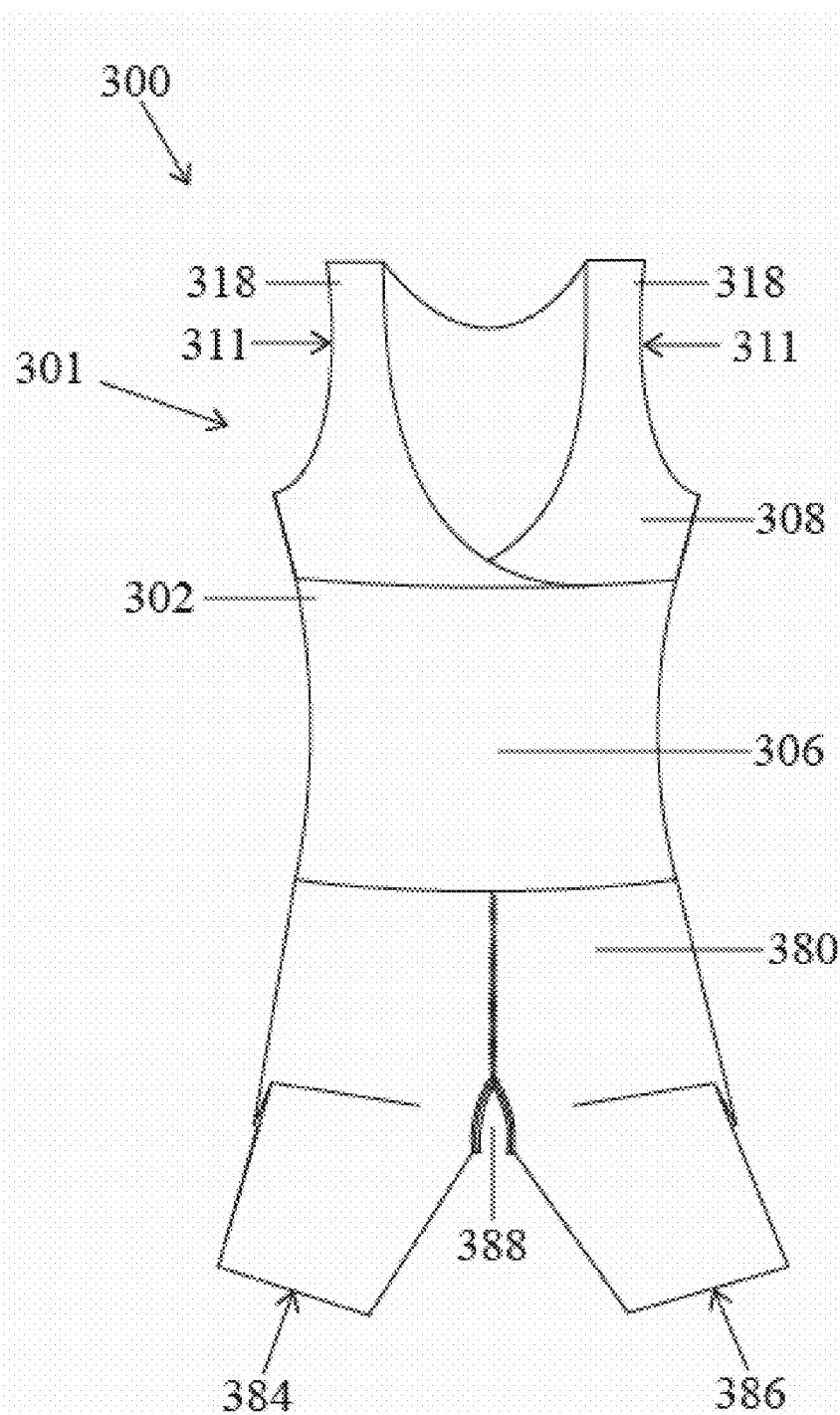
FIG. 11 illustrates a front view of one embodiment of a shapewear garment.
Figure 12:
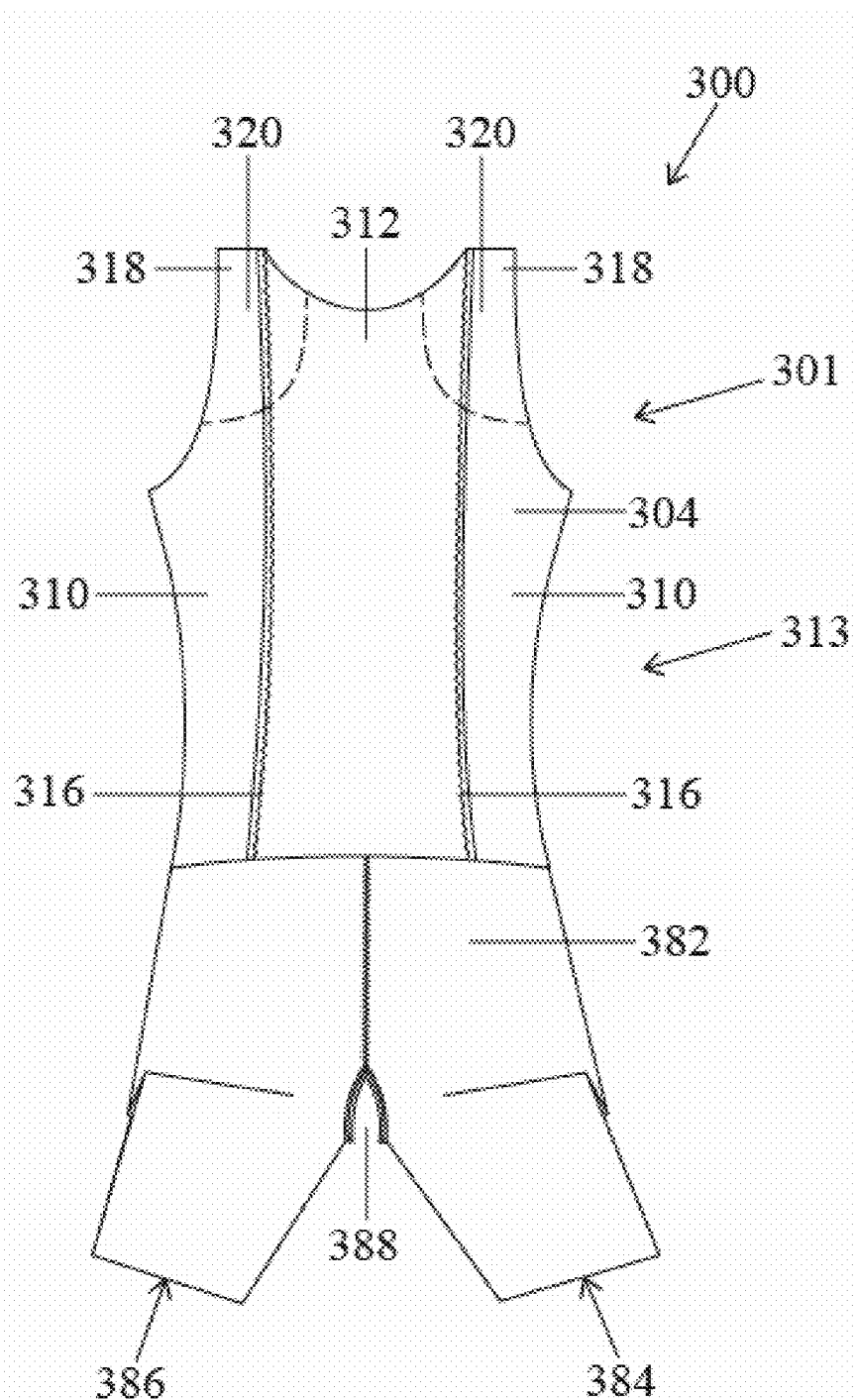
FIG. 12 illustrates a rear view of the shapewear garment of FIG. 11.

FIGS. 11 and 12 illustrate a front and rear view of another embodiment of a shapewear garment 300. The shapewear garment 300 may include a torso body 301 having a front portion 302 and a rear portion 304 that are configured to be positioned on the front and rear portion of a human body, respectively. In some embodiments, the front and rear portions 302, 304 may define a tubular article configured to fit on the torso of a wearer. The front portion of the shapewear garment 300 may include a front torso panel 306 and an upper front torso panel 308. The front torso panel 306 and the upper front torso panel 308 may be made of a stretchable fabric (e.g., 80% nylon and 20% spandex/elastane, etc.). The rear portion 304 may include a back torso panel 313 that includes multiple back torso side panels 310 and a center back princess panel 312. The rear portion 304 may be made of similar or different fabrics from the front portion 302, front torso panel 306, and/or upper front torso panel 308. The front torso panel 306 may be connected to each back torso side panel 310 along a seam. The center back princess panel 312 may be connected to each back torso side panel 310 along a seam 316. The seam 316 may be stitched (e.g., single top zigzag stitch, etc.) to secure the panels to each other while potentially adding decoration and/or extra strength to the shapewear garment 300. The seams 316 may also provide added tension to the front and rear portions.

As shown in FIGS. 11 and 12, the upper front torso panel 308 extends along a shoulder region 311 of the torso body towards the back torso panel 313. The front torso panel 308 and the back torso panel 313 may be attached and combine to define a shoulder strap 318. The shoulder strap 318 may provide a wider shoulder strap region 320 to attach support bands on the rear portion 304 of the torso body 301.

Figure 10:
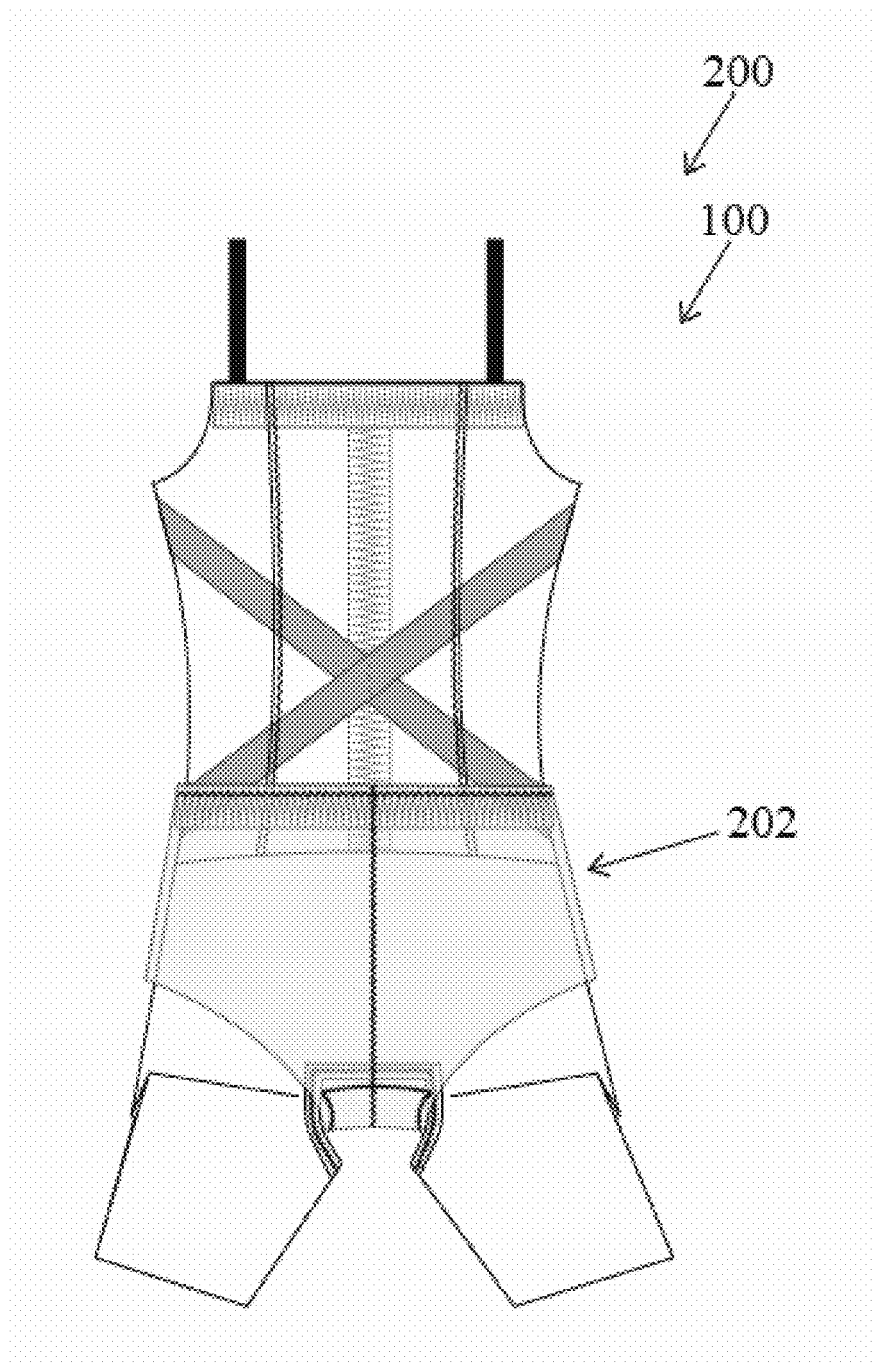
FIG. 10 illustrates a rear view of one embodiment of a shapewear garment and the brief panty placed over the shapewear garment to support the abdomen.
Figure 13:
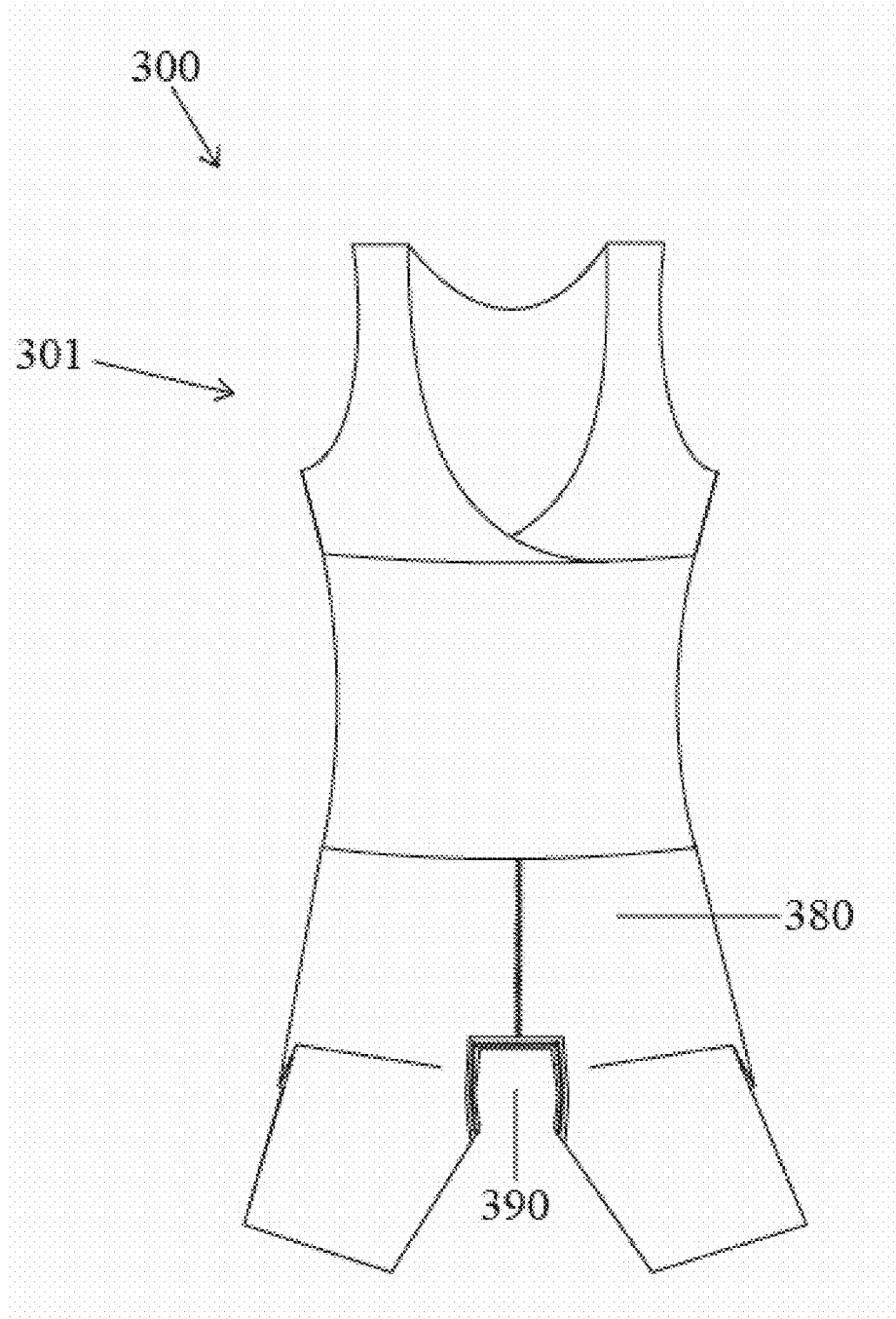
FIG. 13 illustrates a front view of one embodiment of a shapewear garment including a wide opening crotch.
Figure 14:
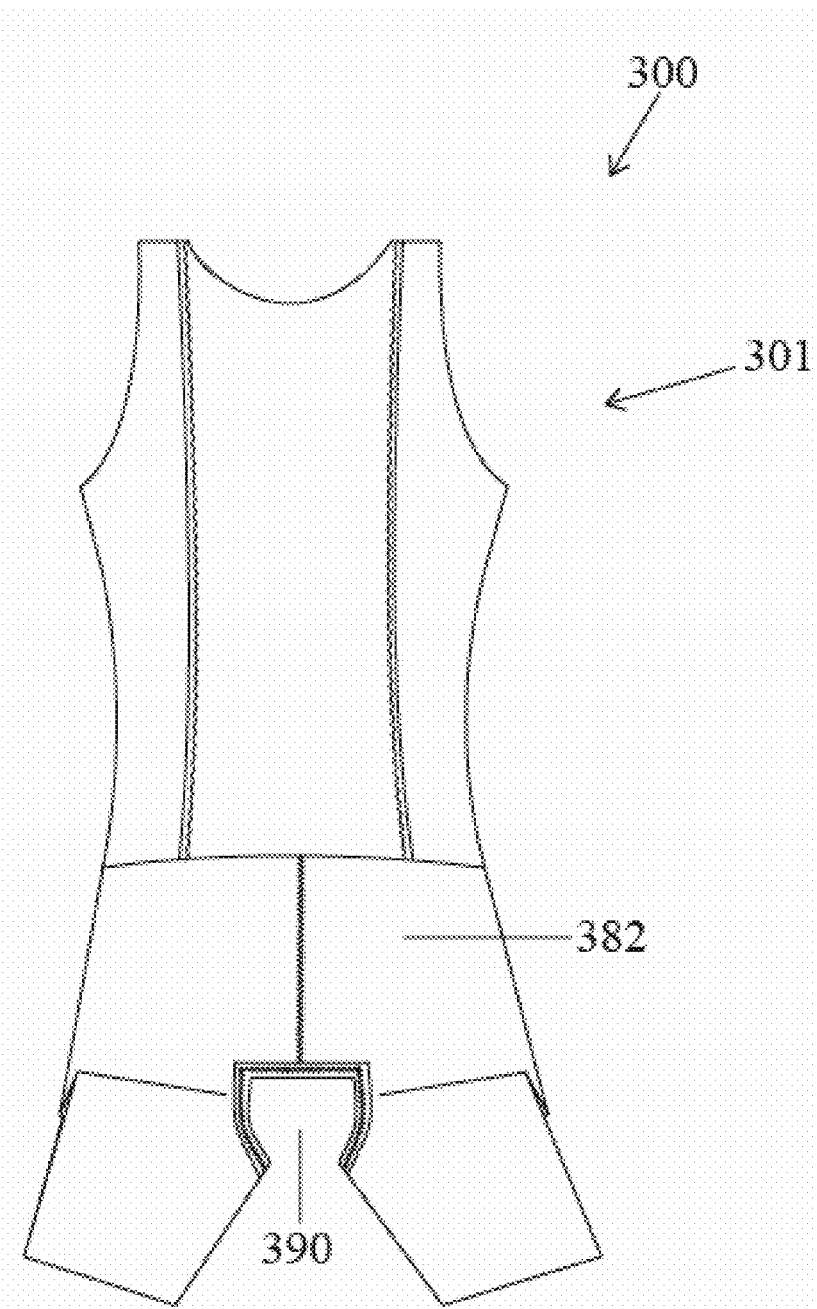
FIG. 14 illustrates a rear view of the shapewear garment of FIG. 13.

As shown in FIGS. 11 and 12, the shapewear garment 300 may include a front bottom panel 380 and a back bottom panel 382. The front and back bottom panels 380, 382 may be attached to the torso panels defining the torso body 301 as described herein. The front and back bottom panels 380, 382 may define a right leg opening 384 and a left leg opening 386. In some embodiments, the front and back bottom panels 380, 382 may define an opening crotch 388 for toileting use. As shown in FIGS. 13 and 14, the shapewear garment 300 may include a wide opening crotch 390. The shapewear garments 300, as shown in FIGS. 13-14 may be configured to be worn with a brief panty (see, e.g., FIGS. 8 and 10).

In some embodiments, the shapewear garment 300 may include four or more support bands. For example, a variety of support band locations are illustrated in FIGS. 15-24. The different support band locations may provide support to an upper spine and shoulder region of a wearer.

Figure 15:
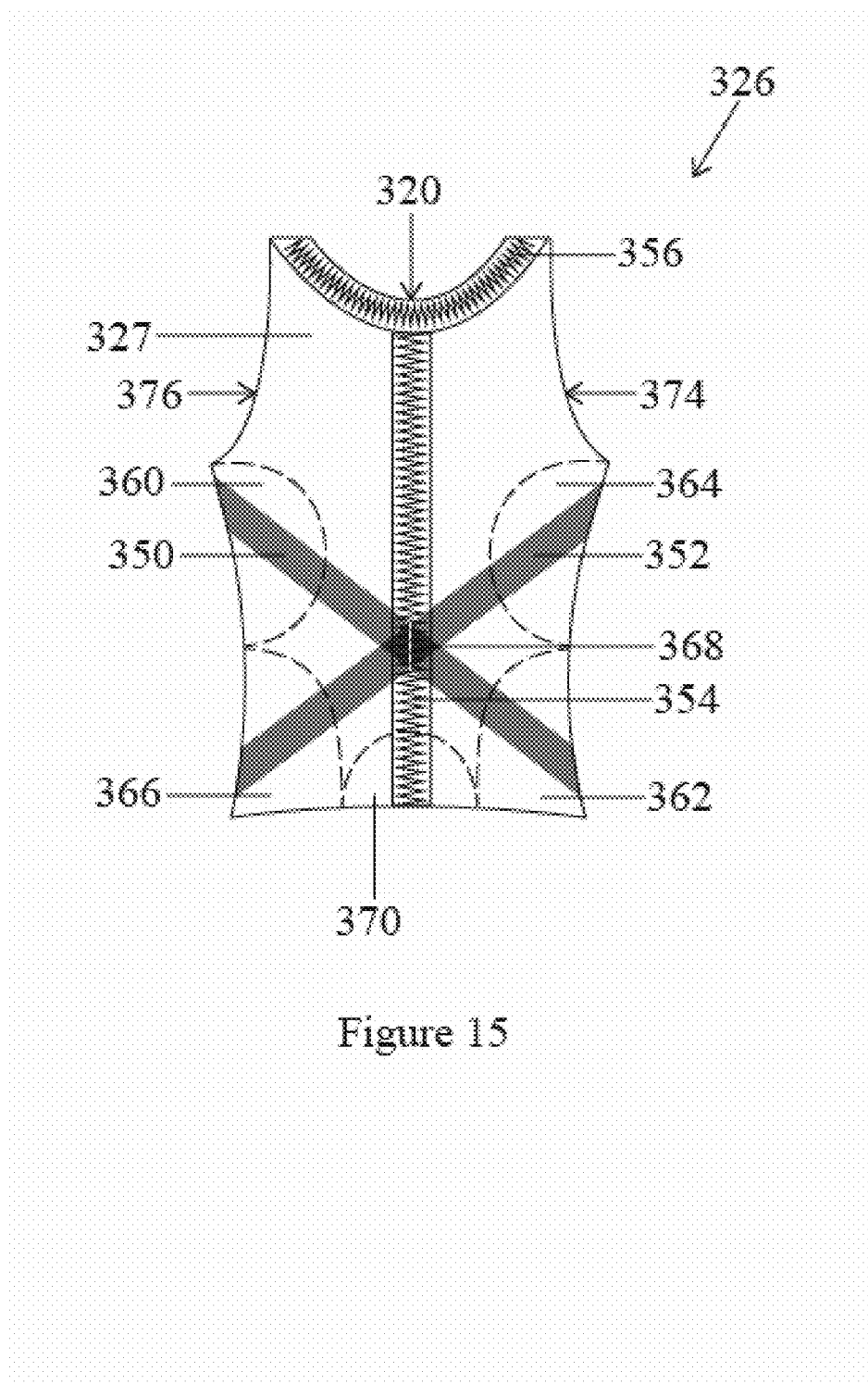
FIG. 15 illustrates an inside view of one embodiment of a back torso lining of a shapewear garment including four support bands.

As shown in FIG. 15, the shapewear garment 300 (e.g., a back torso lining 326) may include a first support band 350, a second support band 352, a third support band 354, and a fourth support band 356. In this example, it is illustrated that the support bands are attached to the back torso lining 326 (e.g., an inside 327 thereof), and the back torso lining 326 is then attached to, or inserted into, the rear portion 304 of the torso body 301. However, the support bands can be positioned on the rear portion 304 of the torso body 301 in various manners as described above. The back torso lining 326 is configured to similarly to the back torso lining 126, and therefore the description of the back torso lining 126 herein is incorporated by reference in this example.

The first support band 350 may extend from a left underarm region 360 toward a right waist region 362 on the rear portion 304 of the torso body 301. The second support band 352 may extend from a right underarm region 364 toward a left waist region 366 on the rear portion 304 of the torso body 301. The first and second support bands 350, 352 may intersect at or proximate an intersection point 368. The third support band 354 may extend from the low waist region 370 toward the neck opening 320 on the rear portion of the torso body. In some embodiments, the third support band 354 may be oriented such that the third support band 354 is substantially vertical when a wearer is standing upright. The fourth support band 356 may extend along the neck opening 320 between the right and left arm openings 374, 376 on the rear portion of the torso body. In one or more embodiments in which the fourth support band 356 is curved, the third support band 354 may be transverse to a tangent of the curve defined by the fourth support band 356 at the intersection (real or imaginary) of the third support band 354 and the fourth support band 356.

Figure 16:
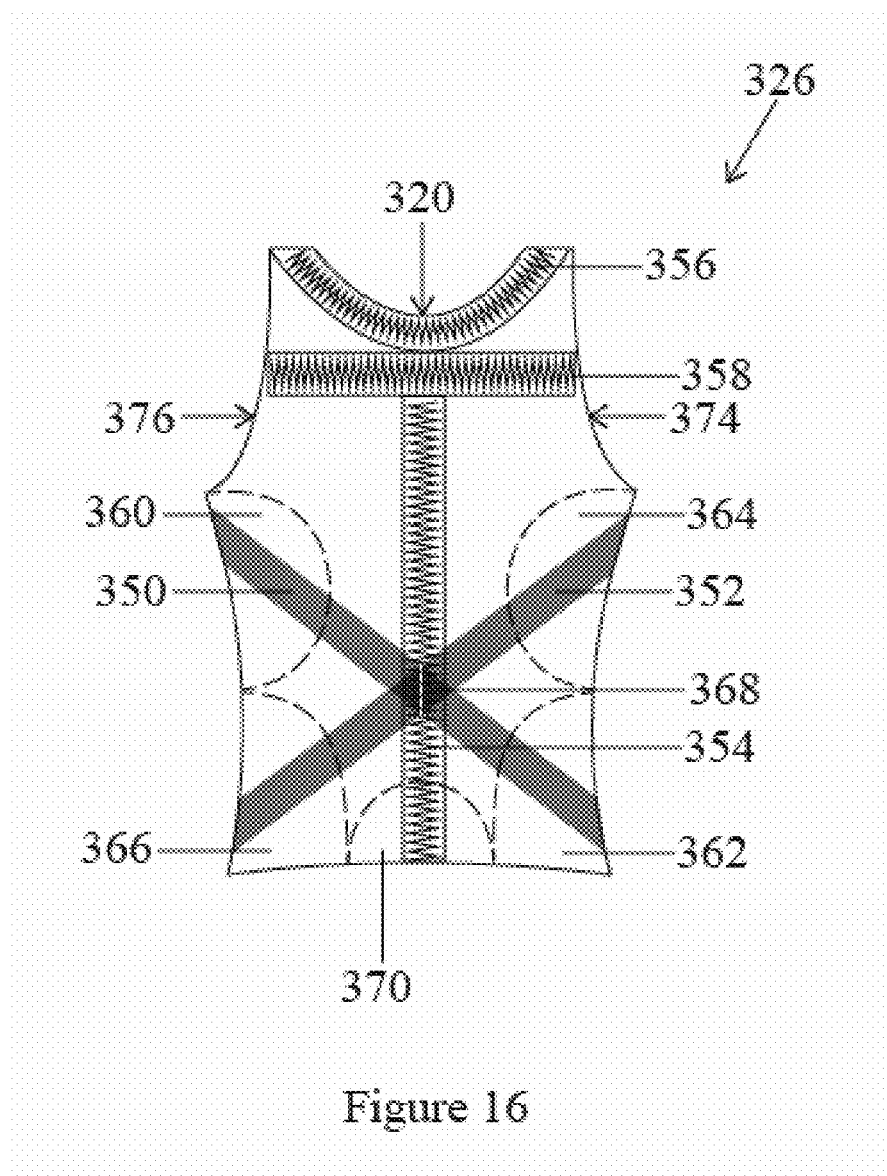
FIG. 16 illustrates an inside view of one embodiment of a back torso lining of a shapewear garment including five support bands.

As shown in FIG. 16, the shapewear garment 300 (e.g., the back torso lining 326) may include a first support band 350, a second support band 352, a third support band 354, a fourth support band 356, and a fifth support band 358. The first support band 350 may extend from the left underarm region 360 toward the right waist region 362 on the rear portion 304 of the torso body 301. The second support band 352 may extend from the right underarm region 364 toward the left waist region 366 on the rear portion 304 of the torso body 301. The first and second support bands 350, 352 may intersect at or proximate an intersection point 368. The third support band 354 may extend from the low waist region 370 toward the neck opening 320 on the rear portion of the torso body. In some embodiments, the third support band 370 may be oriented such that the third support band 354 is substantially vertical when a wearer is standing upright. The fifth support band 358 may extend between the right and left arm openings 374, 376 on the rear portion 304 of the torso body 301. As shown, the fifth support band 358 may be oriented such that the fifth support band 358 is substantially horizontal when a wearer is standing upright. The fourth support band 356 may extend along the neck opening 320 between the right and left arm openings 374, 376 on the rear portion 304 of the torso body 301. As shown, the fourth support band 356 may be located between the neck opening 320 and the fifth support band 358. In one or more embodiments in which the fourth support band 356 is curved, the third support band 354 may be transverse to a tangent of the curve defined by the fourth support band 356 at the intersection (real or imaginary) of the third support band 354 and the fourth support band 356. In one or more embodiments in which the fifth support band 358 is straight, the third support band 354 may be transverse to the fifth support band 358.

Figure 17:
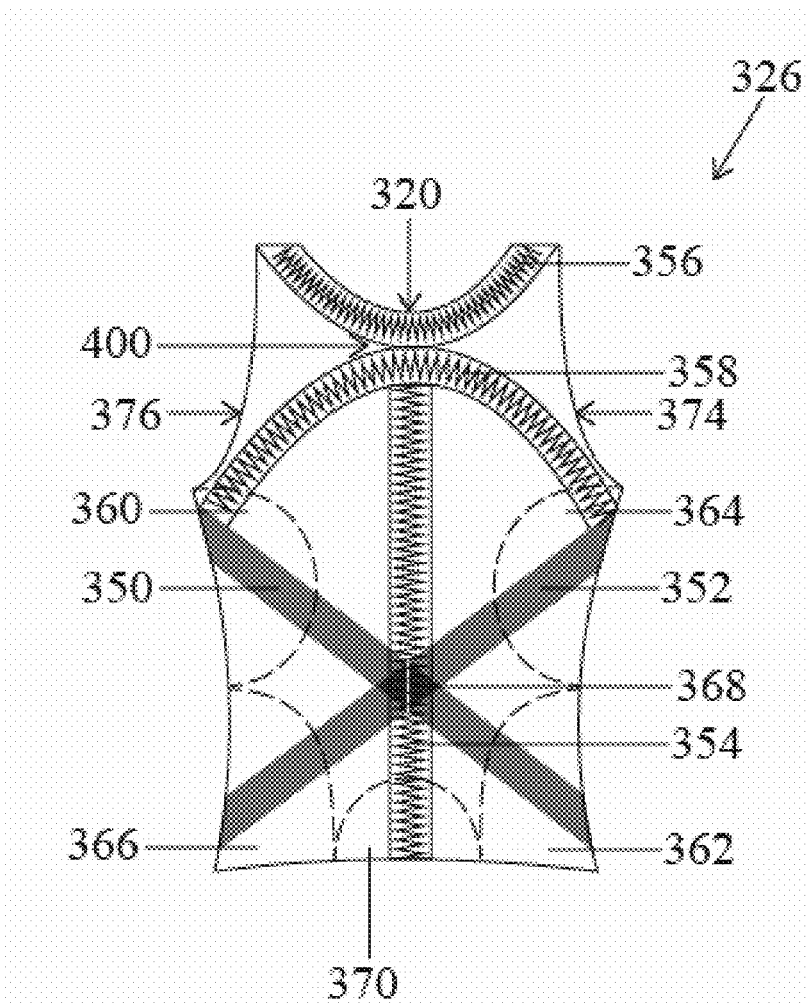
FIG. 17 illustrates an inside view of one embodiment of a back torso lining of a shapewear garment including five support bands.

As shown in FIG. 17, the shapewear garment 300 (e.g., the back torso lining 326) may include a first support band 350, a second support band 352, a third support band 354, a fourth support band 356, and a fifth support band 358. The first support band 350 may extend from the left underarm region 360 toward the right waist region 362 on the rear portion of the torso body. The second support band 352 may extend from the right underarm region 364 toward the left waist region 366 on the rear portion of the torso body. The first and second support bands 350, 352 may intersect at or proximate an intersection point 368. The third support band 354 may extend from the low waist region 370 toward the neck opening 320 on the rear portion of the torso body. In some embodiments, the third support band 354 may be oriented such that the third support band 354 is substantially vertical when a wearer is standing upright. The fifth support band 358 may extend between the right and left arm openings 374, 376 on the rear portion of the torso body. As shown, the fifth support band 358 is defined by a curved shape that extends from the left underarm region 360 toward an apex 400 at or proximate the neck opening 320 and between the left and right arm openings 374, 376 and then toward the right under arm region 364. The fifth support band 358 may help to provide support to the upper shoulder blade region of a wearer. The fourth support band 356 may extend along the neck opening 320 between the right and left arm openings 374, 376 on the rear portion of the torso body. As shown, the fourth support band 356 may be between the neck opening 320 and the fifth support band 358.

Figure 18:
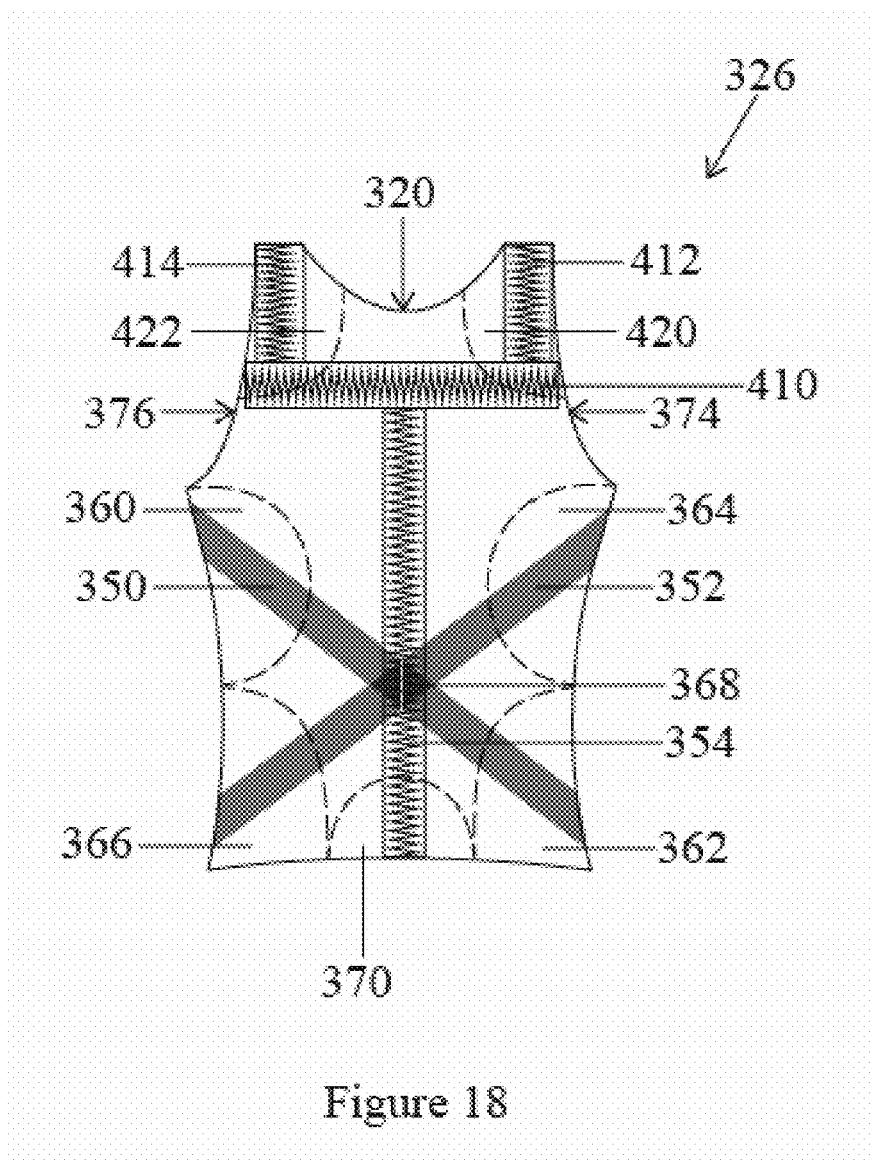
FIG. 18 illustrates an inside view of one embodiment of a back torso lining of a shapewear garment including six support bands.

As shown in FIG. 18, the shapewear garment 300 (e.g., the back torso lining 326) may include a first support band 350, a second support band 352, a third support band 398, a fourth support band 410, a fifth support band 412, and a sixth support band 414. The first support band 350 may extend from the left underarm region 360 toward the right waist region 362 on the rear portion 304 of the torso body 301. The second support band 352 may extend from the right underarm region 364 toward the left waist region 366 on the rear portion 304 of the torso body 301. The first and second support bands 350, 352 may intersect at or proximate an intersection point 368. The third support band 354 may extend from the low waist region 370 toward the neck opening 320 on the rear portion 304 of the torso body 301. In some embodiments, the third support band 354 may be oriented such that the third support band 354 is substantially vertical when a wearer is standing upright. The fourth support band 410 may extend between the right and left arm openings 374, 376 on the rear portion 304 of the torso body 301. As shown, the fourth support band 410 may be oriented such that the fourth support band 410 is substantially horizontal when a wearer is standing upright. The fifth support band 412 may extend from the fourth support band 410 toward a right shoulder strap region 420 of the torso body 301. The sixth support band 414 may extend from the fourth support band 410 toward a left shoulder strap region 422 of the torso body 301. The left shoulder strap region 422 may be a location between the left arm opening 376 of the torso body 301 and the neck opening 320 of the torso body 301 and the right shoulder strap region 374 may be a location between the right arm opening 374 of the torso body 301 and the neck opening 320 of the torso body 301. As shown, the fifth and sixth support bands 412, 414 may be transverse to the fourth support band 410.

Figure 19:
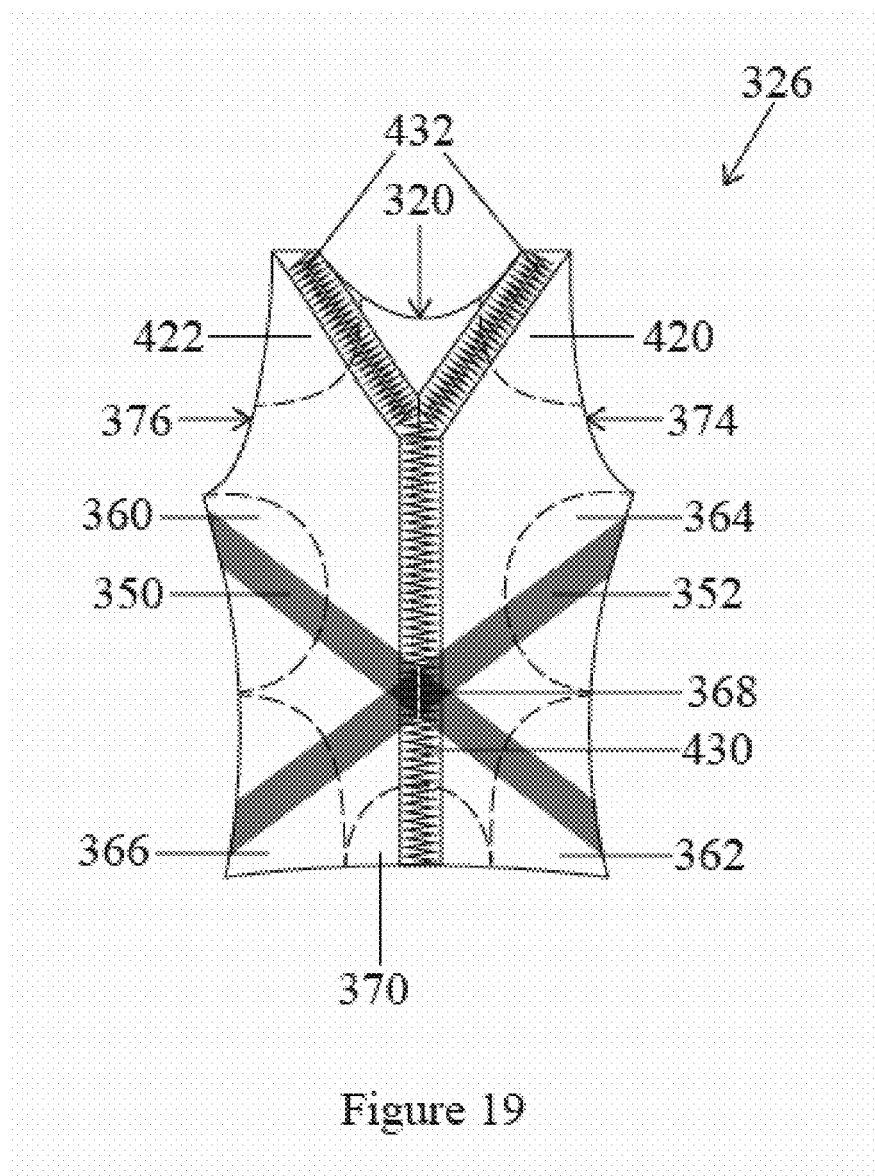
FIG. 19 illustrates an inside view of one embodiment of a back torso lining of a shapewear garment including four support bands.

As shown in FIG. 19, the shapewear garment 300 (e.g., the back torso lining 326) may include a first support band 350, a second support band 352, a third support band 430, and a fourth support band 432. The first support band 350 may extend from the left underarm region 360 toward the right waist region 362 on the rear portion 304 of the torso body 301. The second support band 352 may extend from the right underarm region 364 toward the left waist region 366 on the rear portion 304 of the torso body 301. The first and second support bands 350, 352 may intersect at or proximate an intersection point 368. The third support band 430 may extend from the low waist region 370 toward the neck opening 320 on the rear portion 304 of the torso body 301. In some embodiments, the third support band 430 may be oriented such that the third support band 430 is substantially vertical when a wearer is standing upright. The fourth support band 432 may extend from a left shoulder strap region 422 toward a location at or proximate the third support band 430 and then toward a right shoulder strap region 420. The fourth support band 432 may define a V-shape and the point of the V-shape may be located at or proximate the third support band 430. The left shoulder strap region 422 may be a location between the left arm opening 376 of the torso body 301 and the neck opening 320 of the torso body 301 and the right shoulder strap region 420 may be a location between the right arm opening 374 of the torso body 301 and the neck opening 320 of the torso body 301. A combination of the V-shape of the fourth support band 432 and the third support band 430 may define a Y-shape.

Figure 20:
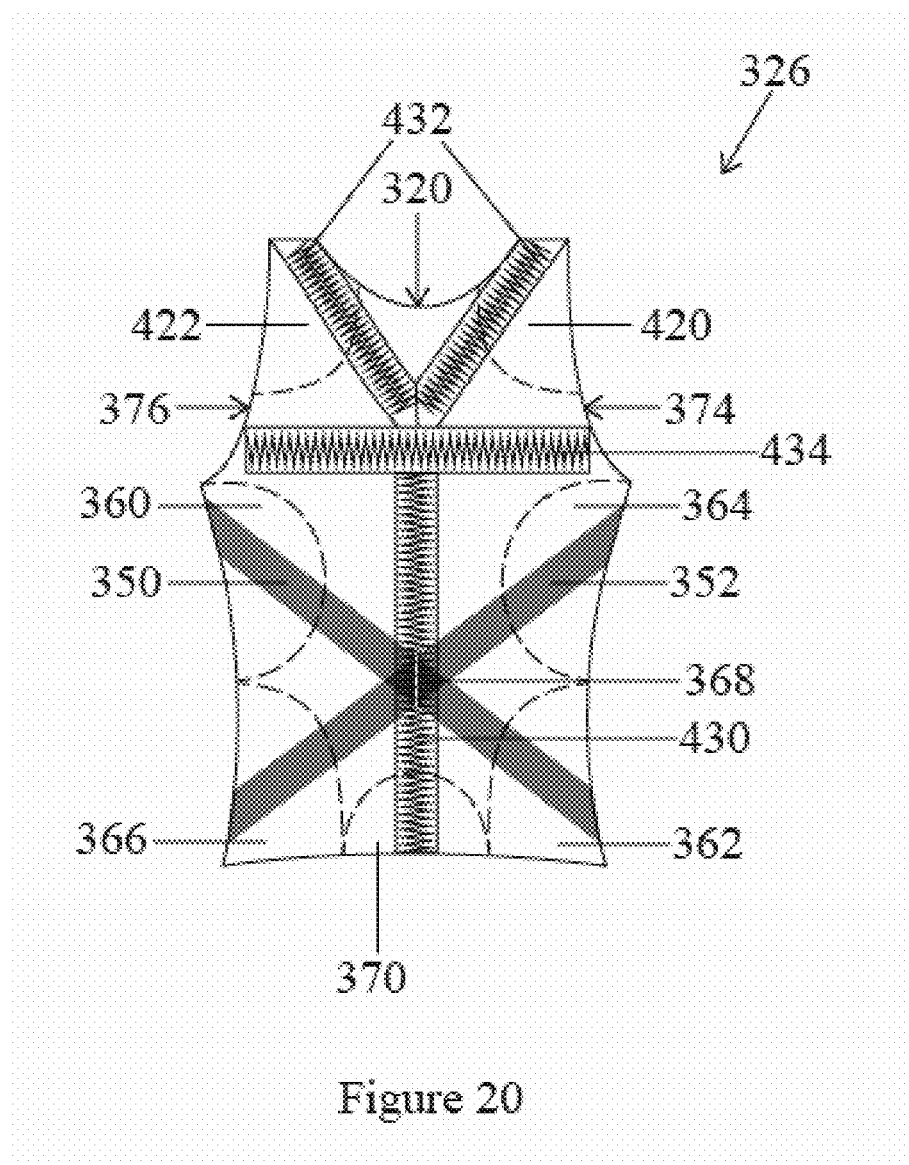
FIG. 20 illustrates an inside view of one embodiment of a back torso lining of a shapewear garment including five support bands.

As shown in FIG. 20, the shapewear garment 300 (e.g., the back torso lining 326) may include a first support band 350, a second support band 352, a third support band 430, a fourth support band 432, and a fifth support band 434. The first support band 350 may extend from the left underarm region 360 toward the right waist region 362 on the rear portion 304 of the torso body 301. The second support band 352 may extend from the right underarm region 364 toward the left waist region 366 on the rear portion 304 of the torso body 301. The first and second support bands 350, 352 may intersect at or proximate an intersection point 168. The third support band 430 may extend from the low waist region 370 toward the neck opening 320 on the rear portion 304 of the torso body 301. In some embodiments, the third support band 430 may be oriented such that the third support band 430 is substantially vertical when a wearer is standing upright. The fifth support band 434 may extend between the right and left openings 374, 376 on the rear portion 304 of the torso body 301. As shown, the fifth support band 434 may be oriented such that the fifth support band 434 is substantially horizontal when a wearer is standing upright. The fourth support band 432 may extend from a left shoulder strap region 422 toward a location at or proximate an intersection of the third support band 430 and the fifth support band 434 and then toward a right shoulder strap region 420. The fourth support band 432 may define a V-shape and the point of the V-shape may be located at or proximate the intersection of the third support band 430 and the fifth support band 434. The left shoulder strap region 422 may be a location between the left arm opening 376 of the torso body 301 and the neck opening 320 of the torso body 301 and the right shoulder strap region 420 may be a location between the right arm opening 374 of the torso body 301 and the neck opening 320 of the torso body 301. As shown, the fourth support band 432 may be between the neck opening 320 and the fifth support band 434. A combination of the V-shape of the fourth support band 432 and the third support band 430 may define a Y-shape. The Y-shape and the fifth support band 434 combined may provide support around the upper shoulder blade region of a wearer.

Figure 21:
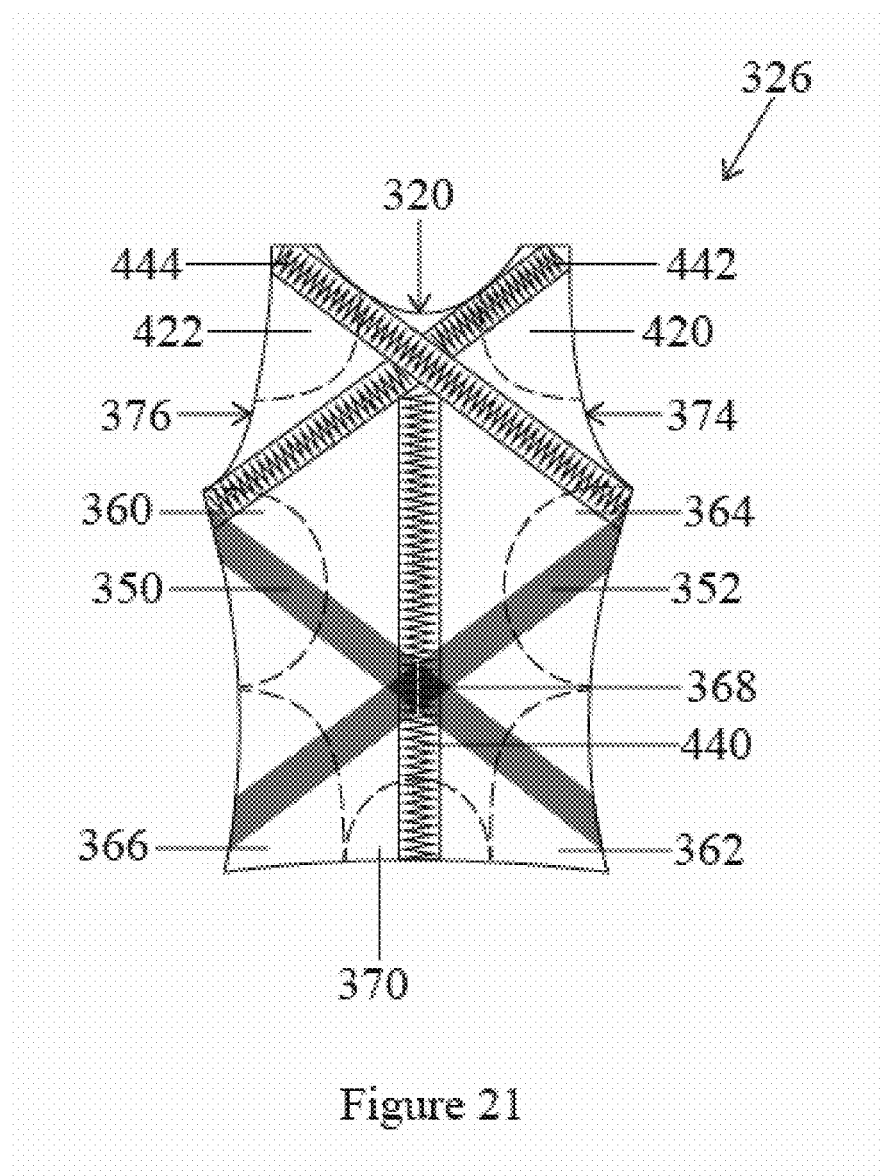
FIG. 21 illustrates an inside view of one embodiment of a back torso lining of a shapewear garment including five support bands.

As shown in FIG. 21, the shapewear garment 300 (e.g., the back torso lining 326) may include a first support band 350, a second support band 352, a third support band 440, a fourth support band 442, and a fifth support band 444. The first support band 350 may extend from the left underarm region 360 toward the right waist region 362 on the rear portion 304 of the torso body 301. The second support band 352 may extend from the right underarm region 364 toward the left waist region 366 on the rear portion 304 of the torso body 301. The first and second support bands 350, 352 may intersect at or proximate an intersection point 368. The third support band 440 may extend from the low waist region 370 toward the neck opening 320 on the rear portion 304 of the torso body 301. In some embodiments, the third support band 440 may be oriented such that the third support band 440 is substantially vertical when a wearer is standing upright. The fourth support band 442 may extend from a right shoulder strap region 420 toward the left underarm region 360. The fifth support band 444 may extend from a left shoulder strap region 442 toward the right underarm region 364. The left shoulder strap region 442 may be a location between the left arm opening 376 of the torso body 301 and the neck opening 320 of the torso body 301 and the right shoulder strap region 440 may be a location between the right arm opening 374 of the torso body 301 and the neck opening 320 of the torso body 301. The fourth support band 442 and the fifth support band 444 may intersect at or proximate a point that is proximate the third support band 440.

Figure 22:
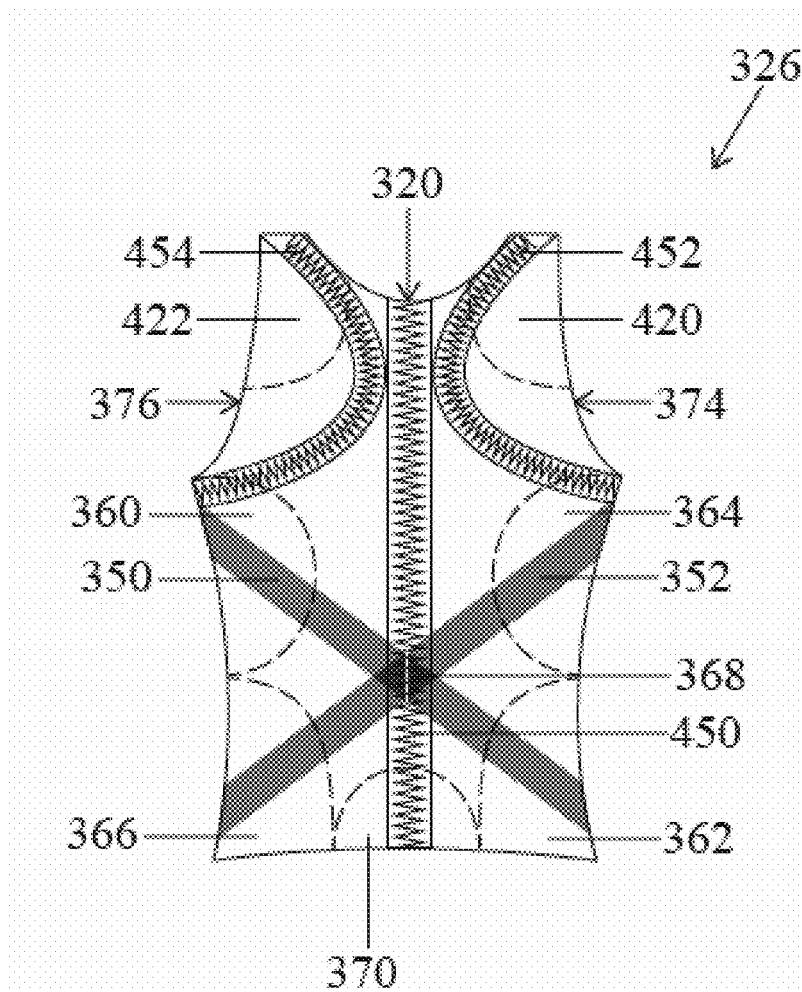
FIG. 22 illustrates an inside view of one embodiment of a back torso lining of a shapewear garment including five support bands.

As shown in FIG. 22, the shapewear garment 300 (e.g., the back torso lining 326) may include a first support band 350, a second support band 352, a third support band 450, a fourth support band 452, and a fifth support band 454. The first support band 350 may extend from the left underarm region 360 toward the right waist region 362 on the rear portion 304 of the torso body 301. The second support band 352 may extend from the right underarm region 364 toward the left waist region 366 on the rear portion 304 of the torso body 301. The first and second support bands 350, 352 may intersect at or proximate an intersection point 368. The third support band 450 may extend from the low waist region 370 toward the neck opening 320 on the rear portion 304 of the torso body 301. In some embodiments, the third support band 370 may be oriented such that the third support band 370 is substantially vertical when a wearer is standing upright. The fourth support band 452 may extend from a right shoulder strap region 420 toward the right underarm region 364. More specifically, the fourth support band 452 may extend from the right shoulder strap region 420 toward the third support band 450 and then toward the right underarm region 364. The fourth support band 452 may be defined by a C-shape opening towards the right. The fifth support band 454 may extend from a left shoulder strap region 422 toward the left underarm 360. More specifically, the fifth support band 454 may extend from the left shoulder strap region 422 toward the third support band 450 and then toward the left under arm region 360. The fifth support band 454 may be defined by a reverse C-shape opening towards the left. In one or more embodiments, the fourth support band 452 and the fifth support band 454 may be mirror images of each other about an axis of symmetry defined along a length of the third support band 450. The left shoulder strap region 422 may be a location between the left arm opening 376 of the torso body 301 and the neck opening 320 of the torso body 301 and the right shoulder strap region 420 may be a location between the right arm opening 374 of the torso body 301 and the neck opening 320 of the torso body 301.

Figure 23:
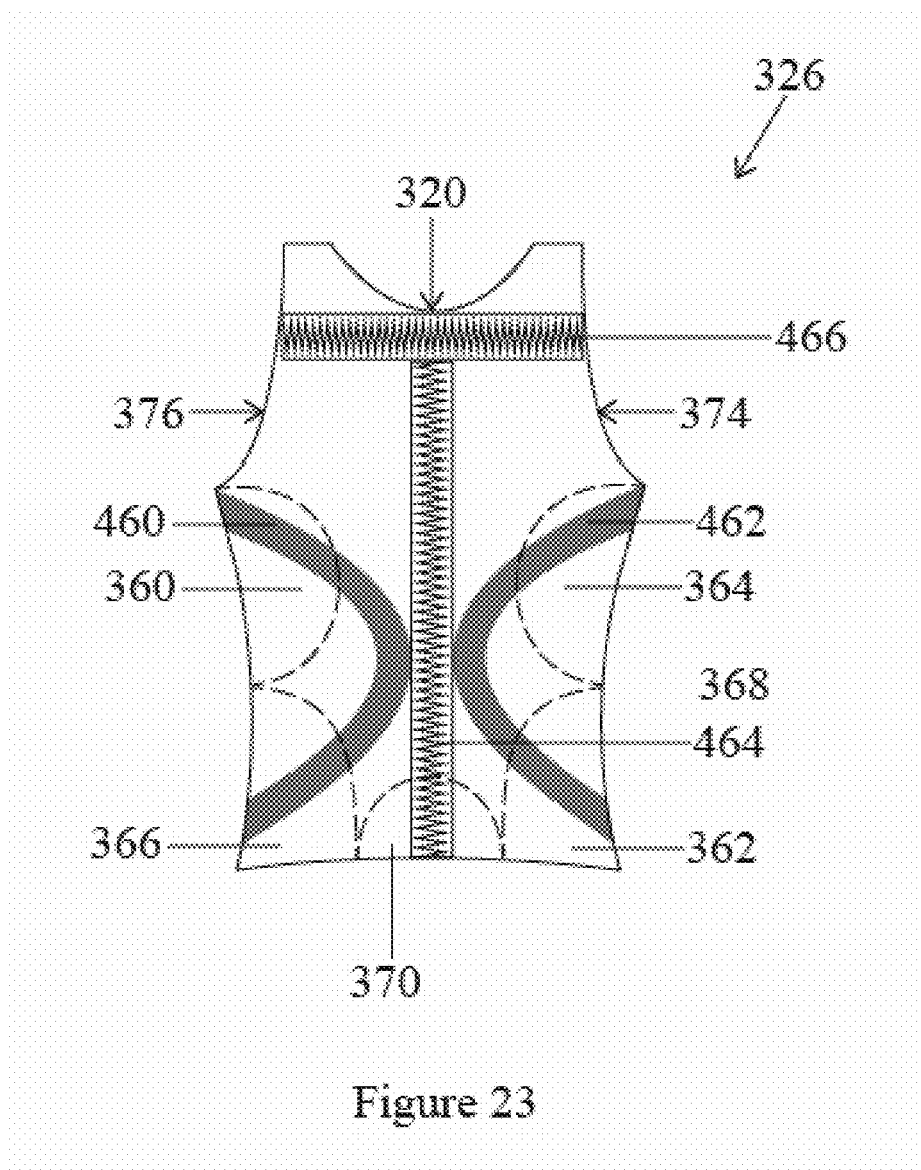
FIG. 23 illustrates an inside view of one embodiment of a back torso lining of a shapewear garment including four support bands.

As shown in FIG. 23, the shapewear garment 300 (e.g., the back torso lining 326) may include a first support band 460, a second support band 462, a third support band 464, and a fourth support band 466. The third support band 464 may extend from the low waist region 370 toward the neck opening 320 on the rear portion 304 of the torso body 301. In some embodiments, the third support band 464 may be oriented such that the third support band 464 is substantially vertical when a wearer is standing upright. The first support band 460 may extend from the left underarm region 360 toward the left waist region 366. More specifically, the first support band 460 may extend from the left underarm region 360 toward the third support band 464 and then toward the left waist region 366 on the rear portion 304 of the torso body 301. The first support band 460 may be defined by a reverse C-shape. The second support band 462 may extend from the right underarm region 364 toward the right waist region 362. More specifically, the second support band 462 may extend from the right underarm region 364 toward the third support band 464 and then toward the right waist region 362 on the rear portion 304 of the torso body 301. The second support band 462 may be defined by a C-shape. The fourth support band 466 may extend between the right and left arm openings 374, 376 on the rear portion 304 of the torso body 301. In one or more embodiments, the C-shapes of the first support band 460 and second support band 462 may approximate an X-shape as defined by, e.g., the first and second support bands 350, 352 of the illustrative embodiments depicted in FIGS. 3A and 15-22. As shown, the fourth support band 466 may be oriented such that the fourth support band 466 is substantially horizontal when a wearer is standing upright. As shown, the third support band 464 and the fourth support band 466 may be transverse to one another.

Figure 24:
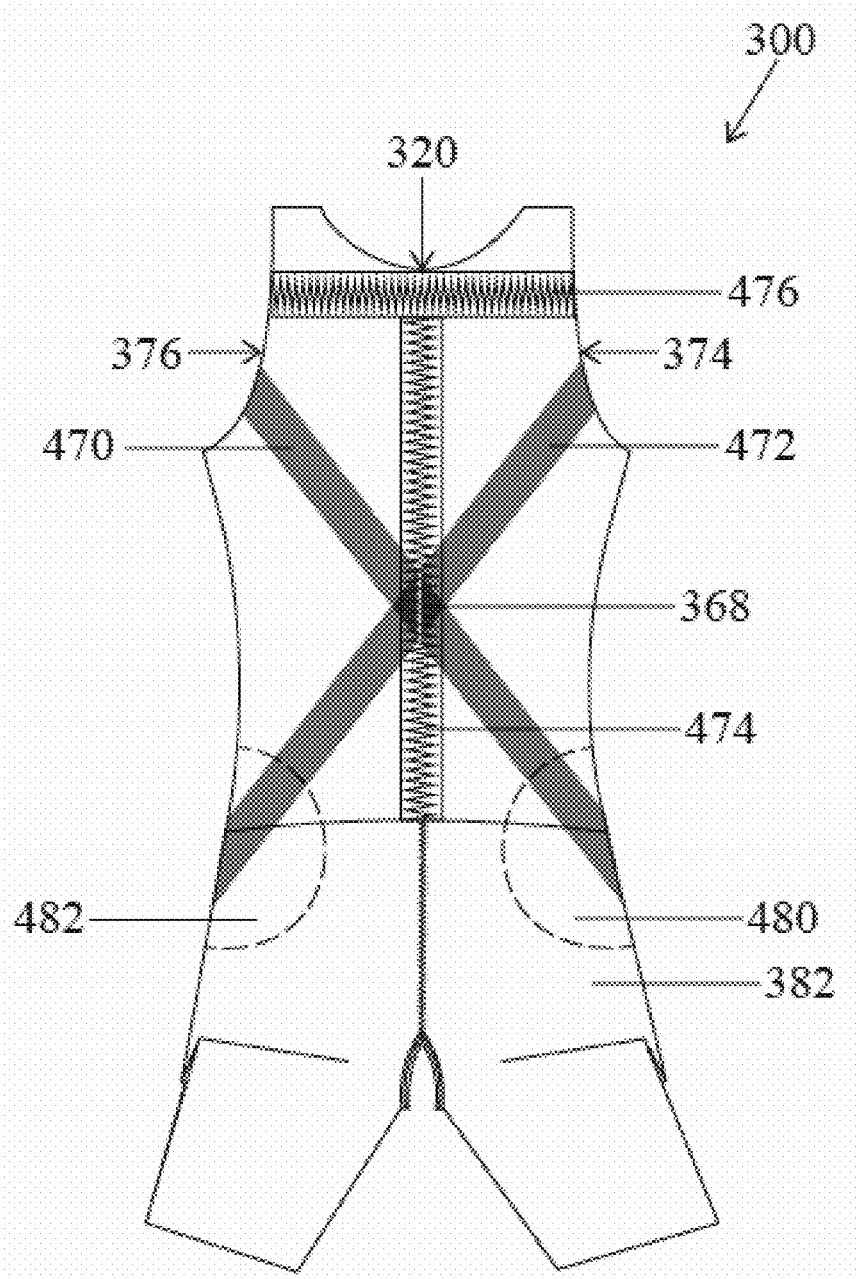
FIG. 24 illustrates an inside view of one embodiment of a back torso lining of a shapewear garment and a bottom panel of the shapewear garment including four support bands.

As shown in FIG. 24, the shapewear garment 300 (e.g., the back torso lining 326) may include a first support band 470, a second support band 472, a third support band 474, and a fourth support band 478. As shown, the first support band 470 may extend from the left arm opening 376 toward a right waist region 480 on the back bottom panel 382. In other embodiments, the first support band 470 may extend from any location from between the neck opening 320 of the torso body 301 and the left arm opening 376 of the torso body to a left waist region 480 of the back bottom panel 382. As shown, the second support band 472 may extend from the right arm opening 372 toward the left waist region 482 on the back bottom panel 382. In other embodiments, the second support band 472 may extend from any location from between the neck opening 320 of the torso body 301 and the right arm opening 374 of the torso body 301 to the right waist region 480 of the back bottom panel 382. The first and second support bands 470, 472 may intersect at or proximate an intersection point 368. In some embodiments, the first and second support bands 470, 472 may be transverse to each other. In other embodiments, the first and second support bands 470, 472 may not be transverse to each other. The third support band 474 may extend from the low waist region 370 toward the neck opening 320 on the rear portion 304 of the torso body 301. In some embodiments, the third support band 474 may be oriented such that the third support band 474 is substantially vertical when a wearer is standing upright. The fourth support band 476 may extend between the right and left arm openings 374, 376 on the rear portion 304 of the torso body 301. As shown, the fourth support band 476 may be oriented such that the fourth support band 476 is substantially horizontal when a wearer is standing upright.

EXAMPLES

The following non-limiting examples serve to describe more fully the manner of using the above described garments and systems. It is understood that these examples in no way serve to limit the scope of this disclosure or claims that follow, but rather are presented for illustrative purposes.

Figure 7A:
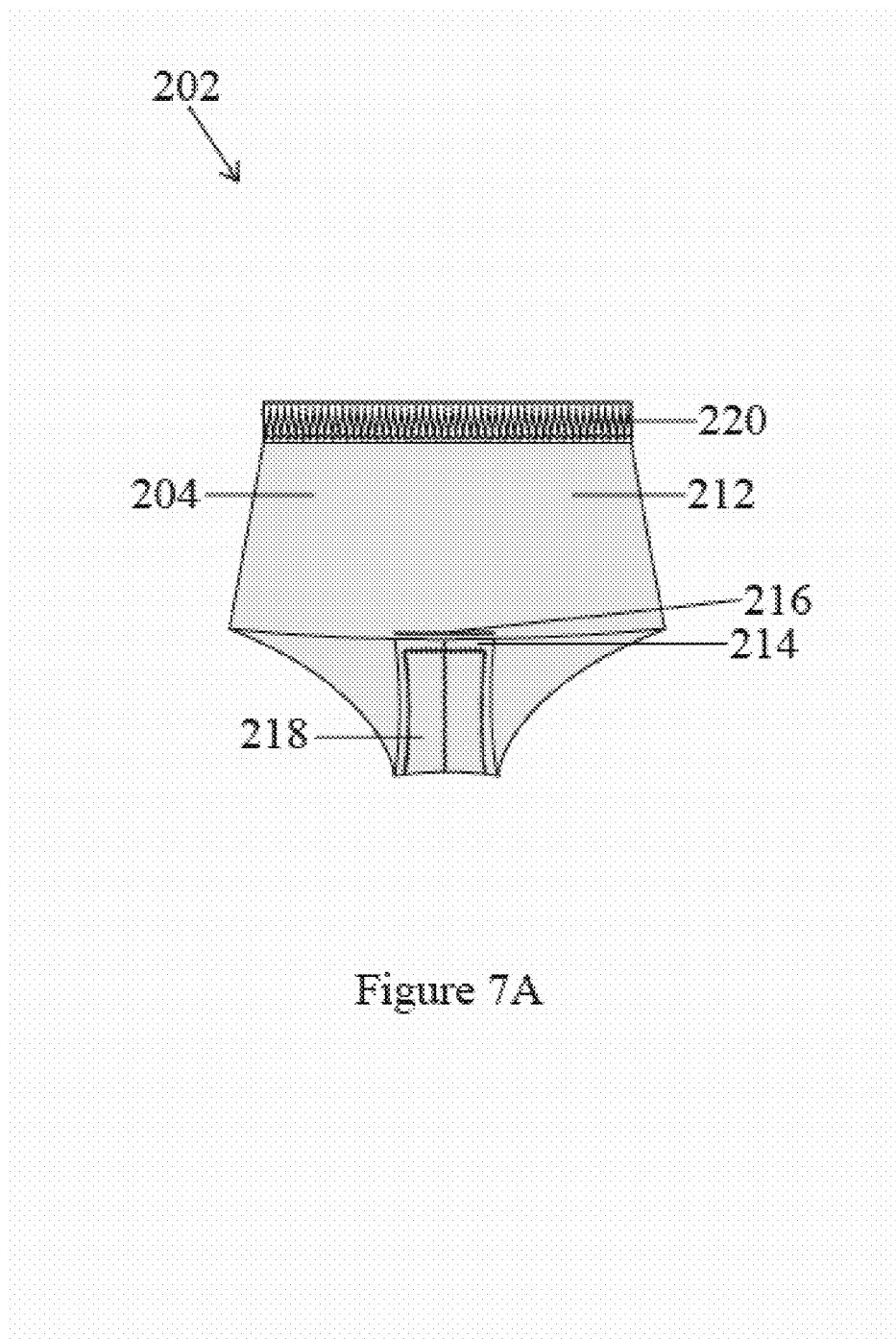
FIG. 7A illustrates a front view of one embodiment of a brief panty to cover the crotch opening of a full-length shapewear garment and including a support waist band to support a waist area.
Figure 7B:
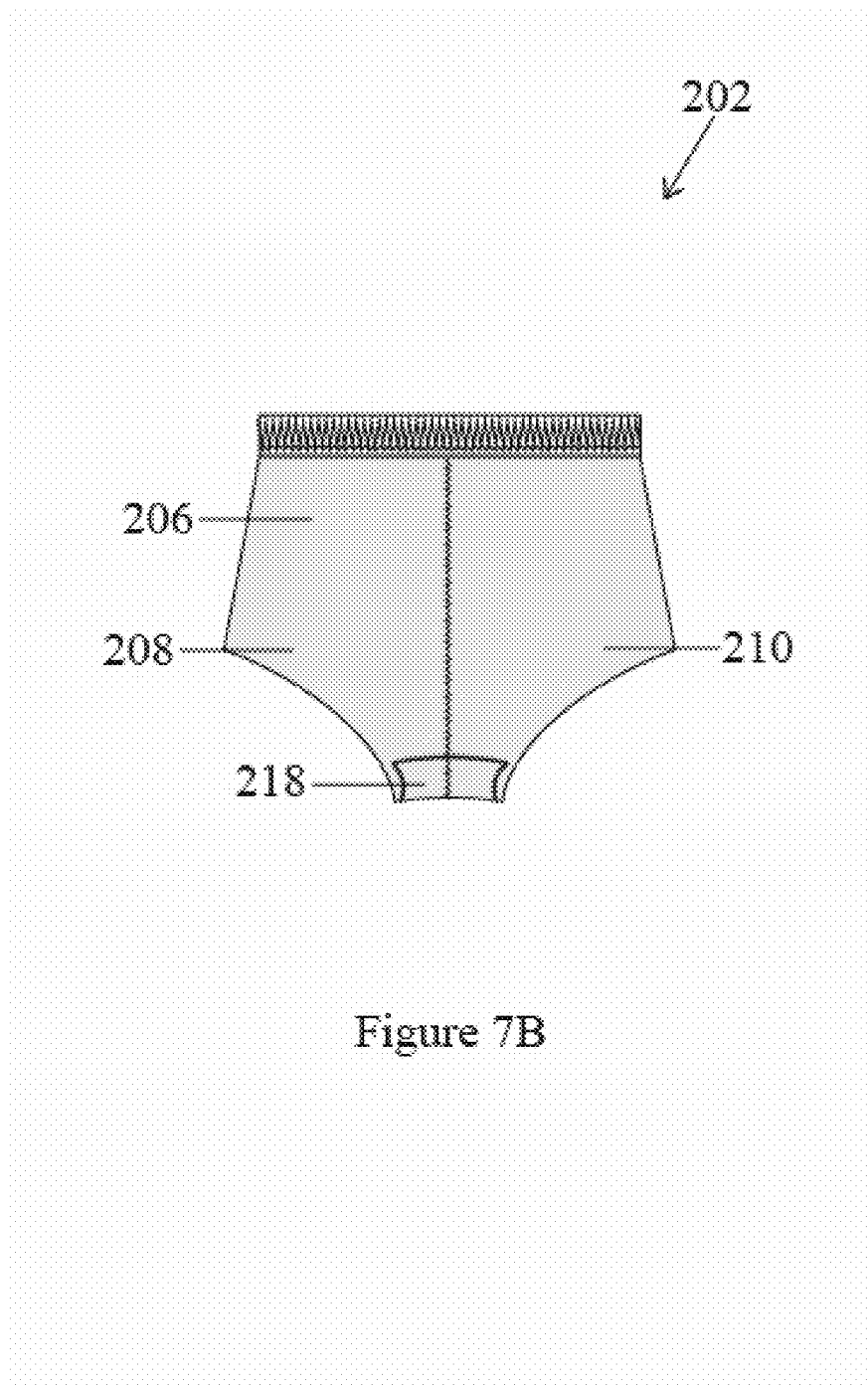
FIG. 7B illustrates a rear view of the brief panty of FIG. 7A.
Figure 25A:
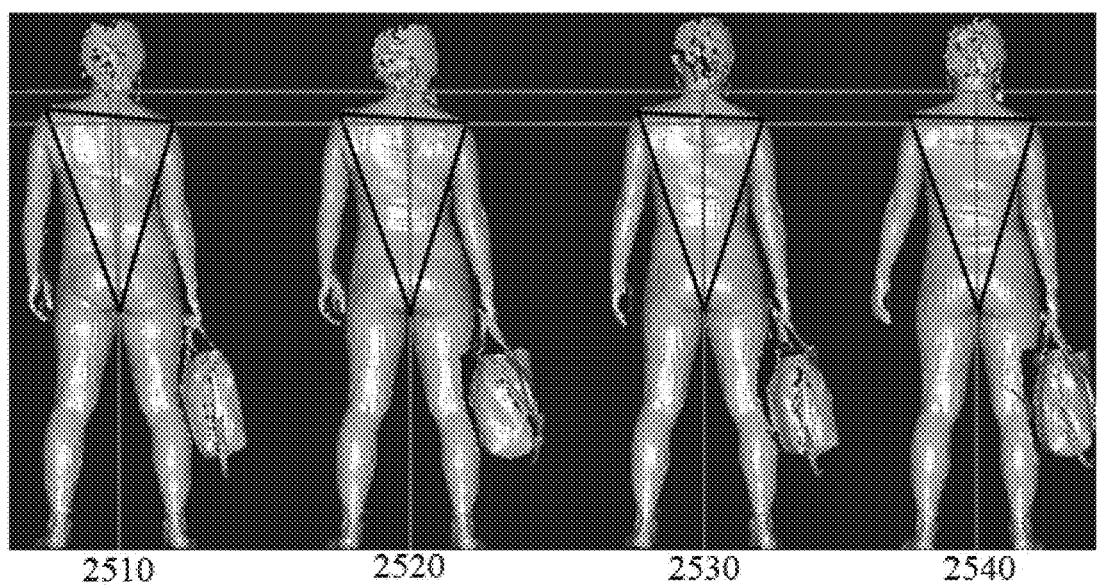
FIG. 25A illustrates a visual analysis scan of one posture from the back of the human body for four different wearing conditions.
Figure 25B:
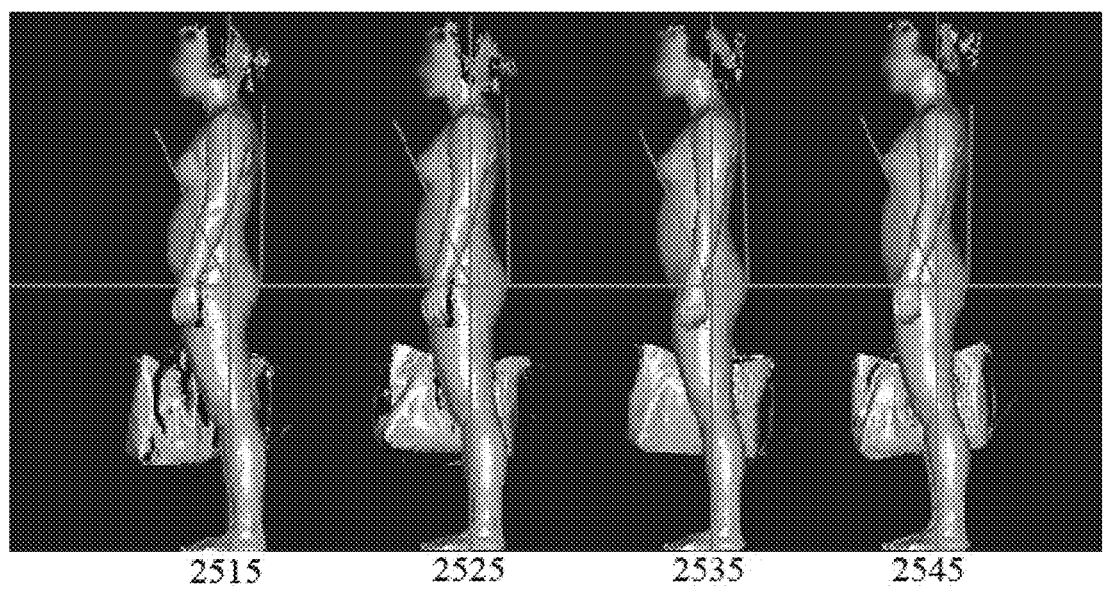
FIG. 25B illustrates a visual analysis scan of one posture from the side of the human body for four different wearing conditions.

A comprehensive test was conducted with 17 women (small, medium, and large size) recruited from university staff, faculty members and students to wear-test the modified shapewear garment including the four support bands as shown in FIGS. 3A-3B. The average age was 21.5 years old for small size group, 20.5 years old for medium size group, and 24 years old for large size group. Participants were scanned three times using a 3D Human Solutions body scanner in: 1. no shapewear garment, 2. the commercial shapewear garment, and 3. the modified shapewear garment. Participants were each scanned wearing their own underwear (bra and panties) in 8 positions including the anatomical pose face forward and feet placed at shoulder width without carrying an item and carrying an item positions including four types of handbags, right-side and left-side loading respectively. One participant was scanned one more time in a garment system as described herein including four support bands as well as a brief panty serving a waist support, as shown in FIGS. 7A, 7B, and 8. After scanning, numerical body angles were calculated using coordinates of some reference points on the 3D scanned body and each angle in the same positions was compared among the three wearing conditions. The test results showed more aligned body angles in the modified shapewear garment compared to the commercial shapewear and no shapewear garment in most cases. It was also observed, in many cases, that the overall shape of the mid-torso was smoother in the shapewear garment of the present disclosure, compared to the commercially available shapewear garment and much smoother than no shapewear garment. FIGS. 25A and 25B illustrate an example showing posture improvement in one of the carrying an item positions on the posterior view and sagittal view, respectively, of one individual in no shapewear garment 2510, 2515, in a commercial shapewear garment 2520, 2525, in the modified shapewear garment 2530, 2535, and in the garment system 2540, 2545.

Since the challenge in developing shapewear garment with posture support elements is to not negatively affect body shape, this is a critical finding indicating a successful shapewear garment design that can help improving posture as well as body shape. The effectiveness of the shapewear garment and the garment system with a simple design element in accordance with present disclosure may indicate that this type of design modification might be applied to any shapewear garment product to prevent poor posture and make more smooth body shape.

Additionally, a shapewear garment may be specifically designed including the design modifications discussed herein to prevent poor posture.

In a first aspect, one or more embodiments of the shapewear garments described herein include a torso body comprising a front portion and a rear portion, wherein the torso body defines: a neck opening, a right arm opening, a left arm opening, a right leg opening, a left leg opening, a waist region located around the torso body and between the arm openings and the leg openings, wherein the waist region comprises a left waist region, a right waist region, and a low waist region between the left and right waist regions, a right underarm region located between the right arm opening and the right leg opening, wherein the right underarm region is closer to the right arm opening than the right leg opening, and a left underarm region located between the left arm opening and the left leg opening, wherein the left under arm region is closer to the left arm opening than the left leg opening; a first support band extending from the left underarm region toward the right waist region on the rear portion of the torso body; a second support band extending from the right underarm region toward the left waist region on the rear portion of the torso body, wherein the first support band and the second support band intersect proximate an intersection; a third support band extending from the low waist region toward the neck opening on the rear portion of the torso body; and a fourth support band extending between the right and left arm opening on the rear portion of the torso body.

In a second aspect, one or more embodiments of the shapewear garments described herein include a torso body comprising a front portion and a rear portion, wherein the torso body defines: a neck opening, a right arm opening, a left arm opening, a right leg opening, a left leg opening, a waist region located around the torso body and between the arm openings and the leg openings, wherein the waist region comprises a left waist region, a right waist region, and a low waist region between the left and right waist regions, a right underarm region located between the right arm opening and the right leg opening, wherein the right underarm region is closer to the right arm opening than the right leg opening, and a left underarm region located between the left arm opening and the left leg opening, wherein the left under arm region is closer to the left arm opening than the left leg opening; a first support band extending from the left underarm region toward the right waist region on the rear portion of the torso body; a second support band extending from the right underarm region toward the left waist region on the rear portion of the torso body, wherein the first support band and the second support band intersect proximate an intersection; a third support band extending from the low waist region toward the neck opening on the rear portion of the torso body; a fourth support band extending from a first location between the neck opening and the left arm opening toward a second location between the right arm opening the right leg opening; and a fifth support band extending from a third location between the neck opening and the right arm opening toward a fourth location between the left arm opening and the left leg opening.

In a third aspect according to any one of the preceding aspects, the torso body defines a wide opening crotch.

In a fourth aspect according to any one of the preceding aspects, the intersection of the first and second support bands is closer to the waist region than the neck opening.

In a fifth aspect according to any one of the first through third aspects, the intersection of the first and second support bands is closer to the neck opening than the waist region.

In a sixth aspect according to any one of the preceding aspects, the intersection of the first and second support bands is positioned along the third support band.

In a seventh aspect according to any one of the preceding aspects, the first support band and the second support band are transverse to each other.

In an eighth aspect according to any one of the preceding aspects, the third support band and the fourth support band are transverse to each other.

In a ninth aspect according to any one of the preceding aspects, wherein the support bands have a modulus of elasticity that is greater than a modulus of elasticity of fabric used to construct the portion of the torso body to which they are attached.

In a tenth aspect according to the ninth aspect, wherein at least two of the support bands have different moduli of elasticity.

In an eleventh aspect according to any one of the preceding aspects, the third support band extends between the low waist region and a center of the neck opening on the rear portion of the torso body.

In a twelfth aspect according to the first aspect, the fourth support band extends along the neck opening on the rear portion of the torso body.

In a thirteenth aspect according to the first aspect, the garment further comprises a fifth support band extending along the neck opening on the rear portion of the torso body.

In a fourteenth aspect according to the first aspect, the garment further comprises a fifth support band on the rear portion of the torso body.

In a fifteenth aspect according to the first aspect, the garment further comprises a fifth support band and a sixth support band on the rear portion of the torso body, wherein the fifth and sixth support bands are transverse to the fourth support band.

In a sixteenth aspect, one or more embodiments of the shapewear garment systems described herein include a garment of any one of the first through fifteenth aspects; and a brief panty, wherein the brief panty comprises a waist support band positioned around a waist of the brief panty, and the brief panty defines an inside of the brief panty and an outside of the brief panty.

In a seventeenth aspect according to the sixteenth aspect, the waist support band is folded downward from the waist of the brief panty and on the inside of the brief panty.

The forgoing description, accompanied by drawings that form a part of the description hereof, show illustrations of various embodiments. It is to be understood that other embodiments are contemplated and may be made without departing from the scope of the present disclosure. The detailed description, therefore, is not to be taken in a limiting sense. Also, the various embodiments described herein may be combined to describe additional embodiments.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any number within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

The various examples and teachings described above are provided by way of illustration only and should not be construed to limit the scope of the present disclosure. Those skilled in the art will readily recognize various modifications and changes that may be made without following the example examples and applications illustrated and described herein, and without departing from the true spirit and scope of the present disclosure.

What is claimed is:

1. A garment comprising:
    a torso body having a front portion and a rear portion and including:
        a neck opening;
        a right arm opening;
        a left arm opening;
        a right leg opening;
        a left leg opening;
        a right shoulder strap region;
        a left shoulder strap region;
        a waist region located around the torso body between the arm openings and the leg openings, the waist region including a left waist region, a right waist region, and a low waist region between the left and right waist regions;
        a right underarm region located adjacent the right arm opening between the right arm opening and the right leg opening; and
        a left underarm region located adjacent the left arm opening between the left arm opening and the left leg opening; and
    a plurality of support bands attached to the rear portion of the torso body, each support band extending between (1) one of the neck opening, the right arm opening, the left arm opening, the right leg opening, the left leg opening, the left waist region, the right waist region, the low waist region, the right shoulder strap region, the left shoulder strap region, the right underarm region, and the left underarm region and (2) another of the neck opening, the right arm opening, the left arm opening, the right leg opening, the left leg opening, the left waist region, the right waist region, the low waist region, the right shoulder strap region, the left shoulder strap region, the right underarm region, and the left underarm region,
    wherein at least two of the plurality of support bands intersect at an intersection on the rear portion of the torso body,
    wherein the plurality of support bands includes:
        a first support band extending from the left underarm region toward the right waist region on the rear portion of the torso body;
        a second support band extending from the right underarm region toward the left waist region on the rear portion of the torso body, wherein the first support band and the second support band intersect proximate an intersection;

a third support band extending from the low waist region toward the neck opening on the rear portion of the torso body; and a fourth support band extending from a first location between the right shoulder strap region and the right underarm region toward a second location between the left shoulder strap region and the left underarm region on the rear portion of the torso body, wherein the fourth support band extends along the neck opening on the rear portion of the torso body.

2. The garment of claim 1, wherein the torso body includes a wide opening crotch.

3. The garment of claim 1, wherein the support bands have a modulus of elasticity that is greater than a modulus of elasticity of fabric used to construct the portion of the torso body to which they are attached.

4. The garment of claim 3, wherein at least two of the support bands have different moduli of elasticity.

5. The garment of claim 1, wherein the first support band and the second support band are transverse to each other.

6. The garment of claim 1, wherein the intersection of the support bands is positioned along the third support band on the rear portion of the torso body.

7. The garment of claim 1, wherein the third support band extends between the low waist region and a center of the neck opening on the rear portion of the torso body.

8. The garment of claim 1, wherein the third support band and the fourth support band are transverse to each other.

9. The garment of claim 1, wherein the intersection of the first, second, and third support bands is closer to the waist region than the neck opening on the rear portion of the torso body.

10. The garment of claim 1, further comprising a fifth support band on the rear portion of the torso body, wherein the fourth support band is located between the neck opening and the fifth support band.

11. The garment of claim 1, further comprising a fifth support band and a sixth support band on the rear portion of the torso body, wherein the fifth and sixth support bands are transverse to the fourth support band.

12. A garment comprising:

a torso body having a front portion and a rear portion and including:
- a neck opening;
- a right arm opening;
- a left arm opening;
- a right leg opening;
- a left leg opening;
- a right shoulder strap region;
- a left shoulder strap region;
- a waist region located around the torso body between the arm openings and the leg openings, the waist region including a left waist region, a right waist region, and a low waist region between the left and right waist regions;
- a right underarm region located adjacent the right arm opening between the right arm opening and the right leg opening; and
- a left underarm region located adjacent the left arm opening between the left arm opening and the left leg opening; and a plurality of support bands attached to the rear portion of the torso body, each support band extending between (1) one of the neck opening, the right arm opening, the left arm opening, the right leg opening, the left leg opening, the left waist region, the right waist region, the low waist region, the right shoulder strap region, the left shoulder strap region, the right underarm region, and the left underarm region and (2) another of the neck opening, the right arm opening, the left arm opening, the right leg opening, the left leg opening, the left waist region, the right waist region, the low waist region, the right shoulder strap region, the left shoulder strap region, the right underarm region, and the left underarm region, wherein at least two of the plurality of support bands intersect at an intersection on the rear portion of the torso body, wherein the plurality of support bands includes:

a first support band extending from the left underarm region toward the right waist region on the rear portion of the torso body;

a second support band extending from the right underarm region toward the left waist region on the rear portion of the torso body, wherein the first support band and the second support band intersect proximate an intersection;

a third support band extending from the low waist region toward the neck opening on the rear portion of the torso body; and a fourth support band extending from a first location between the right shoulder strap region and the right underarm region toward a second location between the left shoulder strap region and the left underarm region on the rear portion of the torso body, wherein the third support band and the fourth support band are transverse to each other.

13. The garment of claim 12, wherein the torso body includes a wide opening crotch.

14. The garment of claim 12, wherein the support bands have a modulus of elasticity that is greater than a modulus of elasticity of fabric used to construct the portion of the torso body to which they are attached.

15. The garment of claim 12, wherein the first support band and the second support band are transverse to each other.

16. The garment of claim 12, wherein the intersection of the support bands is positioned along the third support band on the rear portion of the torso body.

17. The garment of claim 12, wherein the third support band extends between the low waist region and a center of the neck opening on the rear portion of the torso body.

18. The garment of claim 12, wherein the intersection of the first, second, and third support bands is closer to the waist region than the neck opening on the rear portion of the torso body.

19. The garment of claim 12, further comprising a fifth support band on the rear portion of the torso body, wherein the fourth support band is located between the neck opening and the fifth support band.

20. The garment of claim 12, further comprising a fifth support band and a sixth support band on the rear portion of the torso body, wherein the fifth and sixth support bands are transverse to the fourth support band.

* * * * *